(12) United States Patent
Behl et al.

(10) Patent No.: US 6,900,288 B1
(45) Date of Patent: May 31, 2005

(54) HUMAN SEMAPHORIN 6A-1 (SEMA6A-A), A GENE INVOLVED IN NEURONAL DEVELOPMENT AND REGENERATION MECHANISMS DURING APOPTOSIS, AND ITS USE AS A POTENTIAL DRUG TARGET

(75) Inventors: Christian Behl, München (DE);
Andreas Klostermann, München (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 09/856,681

(22) PCT Filed: Nov. 26, 1999

(86) PCT No.: PCT/EP99/09215

§ 371 (c)(1),
(2), (4) Date: Aug. 3, 2001

(87) PCT Pub. No.: WO00/31252

PCT Pub. Date: Jun. 2, 2000

(30) Foreign Application Priority Data

Nov. 26, 1998 (EP) .............................................. 98122441

(51) Int. Cl.$^7$ ............................ C07K 5/00; C07K 14/00

(52) U.S. Cl. ............................ 530/300; 530/350; 514/2; 514/12

(58) Field of Search ................................ 530/300, 350; 514/2, 12; 435/69.1

(56) References Cited

U.S. PATENT DOCUMENTS

2002/0055627 A1 * 5/2002 Rosen et al. ................ 536/23.5
2003/0003532 A1 * 1/2003 Shimkets .................... 435/69.1
2003/0054514 A1 * 3/2003 Shimkets et al. ........... 435/183

FOREIGN PATENT DOCUMENTS

| EP | 0 960937 A1 | 1/1999 | |
|---|---|---|---|
| WO | WO 95 07706 A2 | 3/1995 | |
| WO | WO 98 11216 A2 | 3/1998 | |
| WO | WO 98 27205 A2 | 6/1998 | |
| WO | WO 99 32622 A2 | 7/1999 | |
| WO | WO 00/53742 * | 9/2000 | ........... C12N/15/10 |

OTHER PUBLICATIONS

Bork (2000) "Powers and Pitfalls in Sequence Analysis: The 70% Hurdle." Genome Research 10:398–400.*
Skolnick and Fetrow (2000) "From gene to protein structure and function: novel applications of computational approaches in th genomic era." Trends in Biotech. 18(1): 34–39.*
Doerks et al., (Jun. 1998) "Protein annotation: detective work for function prediction." Trends in Genetics 14(6): 248–250.*
Smith and Zhang (Nov. 1997) "The challenges of genome sequence annotation or 'The devil is in the details'." Nature Biotechnology 15:1222–1223.*
Brenner (Apr. 1999) "Errors in genome annotation." Trends in Genetics 15(4): 132–133.*
Bork and Bairoch (Oct. 1996) "Go hunting in sequence databases but watch out for the traps." Trends in Genetics 12(10): 425–427.*
Wells (Sep. 18, 1990) "Additivity of Mutational Effects in Proteins." Biochemistry 29(37): 8509–8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492–495.*
Klostermann et al. (Dec. 15, 2000) The Orthologous Human and Murine Semaphorin 6A–1 Proteins (SEMA6A–1/Sema6A1) ... The Journal of Biological Chemistry 275(50): 39647–39653.*
Culotti, Joseph G., et al., "Functions of Netrins and Semaphorins in Axon Guidance", Current Opinion in Neurobiology, vol. 6, pp. 81–88 (1996).
Gertler, Frank B., et al., "Mena, A Relative of VASP and Drosophila Enabled, Is Implicated in the Control of Microfilament Dynamics", Cell, vol. 87, pp. 227–239 (Oct. 18, 1996).
Hu, Song, et al., "From Membrane to Cytoskeleton: Enabling a Connection", Neuron, vol. 22, pp. 419–422 (Mar. 1999).
Macalma, Teresita, et al., "Molecular Characterization of Human Zyxin", The Journal of Biological Chemistry, vol. 271, No. 49, pp. 31470–31478 (Dec. 6, 1996).
Prehoda, Kenneth, et al., "Structure of the Enabled/VASP Homology 1 Domain–Peptide Complex: A Key Component in the Spatial Control of Actin Assembly", Cell, vol. 97, pp. 471–480 (May 14, 1999).
Willis, Zachary, et al. "The Tyrosine Kinase Abl and Its Substrate Enabled Collaborate with the Receptor Phosohatase Dlar to Control Motor Axon Guidance", Neuron, vol. 22, pp. 301–312 (Feb. 1999).
Zhou, L., et al., "Cloning and expression of a novel murine semaphorin with structural similarity to insect semaphorin I" (Jan. 1997) Molecular and Cellular Neurosciences, vol. 9, pp. 26–41.
Kolodkin, et al., "The semaphorin genes encode a family of transmembrane and secreted growth cone guidance molecules", (Dec. 31, 1993) Cell, vol. 75, pp. 1389–1399.
Hall, K.T., et al., "Human CD100, a novel leukocyte semaphorin that promotes B–cell aggregation and diiferentiation", (Oct. 1996) Proc. Natl. Acad. Sci. USA, vol. 93, pp. 11780–5.

* cited by examiner

Primary Examiner—Elizabeth Kemmerer
Assistant Examiner—Christopher James Nichols
(74) Attorney, Agent, or Firm—Kilpatrick Stockton LLP

(57) ABSTRACT

Human semaphorin 6A-1, a novel gene involved in neuronal development and regeneration mechanisms, is described.

8 Claims, 11 Drawing Sheets

Fig. 1  SEQ ID NO:1

| | |
|---|---:|
| ATGAGGTCAGAAGCCTTGCTGCTATATTTCACACTGCTACACTTTGCTGG | 50 |
| GGCTGGTTTCCCAGAAGATTCTGAGCCAATCAGTATTTCGCATGGCAACT | 100 |
| ATACAAAACAGTATCCGGTGTTTGTGGGCCACAAGCCAGGACGGAACACC | 150 |
| ACACAGAGGCACAGGCTGGACATCCAGATGATTATGATCATGAACGGAAC | 200 |
| CCTCTACATTGCTGCTAGGGACCATATTTATACTGTTGATATAGACACAT | 250 |
| CACACACGGAAGAAATTTATTGTAGCAAAAAACTGACATGGAAATCTAGA | 300 |
| CAGGCCGATGTAGACACATGCAGAATGAAGGGAAAACATAAGGATGAGTG | 350 |
| CCACAACTTTATTAAAGTTCTTCTAAAGAAAAACGATGATGCATTGTTTG | 400 |
| TCTGTGGAACTAATGCCTTCAACCCTTCCTGCAGAAACTATAAGATGGAT | 450 |
| ACATTGGAACCATTCGGGGATGAATTCAGCGGAATGGCCAGATGCCCATA | 500 |
| TGATGCCAAACATGCCAACGTTGCACTGTTTGCAGATGGAAAACTATACT | 550 |
| CAGCCACAGTGACTGACTTCCTTGCCATTGACGCAGTCATTTACCGGAGT | 600 |
| CTTGGAGAAAGCCCTACCCTGCGGACCGTCAAGCACGATTCAAAATGGTT | 650 |
| GAAAGAACCATACTTTGTTCAAGCCGTGGATTACGGAGATTATATCTACT | 700 |
| TCTTCTTCAGGGAAATAGCAGTGGAGTATAACACCATGGGAAAGGTAGTT | 750 |
| TTCCCAAGAGTGGCTCAGGTTTGTAAGAATGATATGGGAGGATCTCAAAG | 800 |
| AGTCCTGGAGAAACAGTGGACGTCGTTCCTGAAGGCGCGCTTGAACTGCT | 850 |
| CAGTTCCTGGAGACTCTCATTTTTATTTCAACATTCTCCAGGCAGTTACA | 900 |
| GATGTGATTCGTATCAACGGGCGTGATGTTGTCCTGGCAACGTTTTCTAC | 950 |
| ACCTTATAACAGCATCCCTGGGTCTGCAGTCTGTGCCTATGACATGCTTG | 1000 |
| ACATTGCCAGTGTTTTTACTGGGAGATTCAAGGAACAGAAGTCTCCTGAT | 1050 |
| TCCACCTGGACACCAGTTCCTGATGAACGAGTTCCTAAGCCCAGGCCAGG | 1100 |
| TTGCTGTGCTGGCTCATCCTCCTTAGAAAGATATGCAACCTCCAATGAGT | 1150 |
| TCCCTGATGATACCCTGAACTTCATCAAGACGCACCCGCTCATGGATGAG | 1200 |
| GCAGTGCCCTCCATCTTCAACAGGCATGGTTCCTGAGAACAATGGTCAG | 1250 |
| ATACCGCCTTACCAAAATTGCAGTGGACACAGCTGCTGGGCCATATCAGA | 1300 |
| ATCACACTGTGGTTTTTCTGGGATCAGAGAAGGGAATCATCTTGAAGTTT | 1350 |
| TTGGCCAGAATAGGAAATAGTGGTTTTCTAAATGACAGCCTTTTCCTGGA | 1400 |
| GGAGATGAGTGTTTACAACTCTGAAAAATGCAGCTATGATGGAGTCGAAG | 1450 |
| ACAAAAGGATCATGGGCATGCAGCTGGACAGAGCAAGCAGCTCTCTGTAT | 1500 |
| GTTGCGTTCTCTACCTGTGTGATAAAGGTTCCCCTTGGCCGGTGTGAACG | 1550 |
| ACATGGGAAGTGTAAAAAAACCTGTATTGCCTCCAGAGACCCATATTGTG | 1600 |
| GATGGATAAAGGAAGGTGGTGCCTGCAGCCATTTATCACCCAACAGAGA | 1650 |

Fig. 1 (cont.)

| Sequence | Position |
|---|---|
| CTGACTTTTGAGCAGGACATAGAGCGTGGCAATACAGATGGTCTGGGGGA | 1700 |
| CTGTCACAATTCCTTTGTGGCACTGAATGGGCATTCCAGTTCCCTCTTGC | 1750 |
| CCAGCACAACCACATCAGATTCGACGGCTCAAGAGGGGTATGAGTCTAGG | 1800 |
| GGAGGAATGCTGGACTGGAAGCATCTGCTTGACTCACCTGACAGCACAGA | 1850 |
| CCCTTTGGGGGCAGTGTCTTCCCATAATCACCAAGACAAGAAGGGAGTGA | 1900 |
| TTCGGGAAAGTTACCTCAAAGGCCACGACCAGCTGGTTCCCGTCACCCTC | 1950 |
| TTGGCCATTGCAGTCATCCTGGCTTTCGTCATGGGGCCGTCTTCTCGGG | 2000 |
| CATCACCGTCTACTGCGTCTGTGATCATCGGCGCAAAGACGTGGCTGTGG | 2050 |
| TGCAGCGCAAGGAGAAGGAGCTCACCCACTCGCGCCGGGGCTCCATGAGC | 2100 |
| AGCGTCACCAAGCTCAGCGGCCTCTTTGGGGACACTCAATCCAAAGACCC | 2150 |
| AAAGCCGGAGGCCATCCTCACGCCACTCATGCACAACGGCAAGCTCGCCA | 2200 |
| CTCCCGGCAACACGGCCAAGATGCTCATTAAAGCAGACCAGCACCACCTG | 2250 |
| GACCTGACGGCCCTCCCCACCCCAGAGTCAACCCCAACGCTGCAGCAGAA | 2300 |
| GCGGAAGCCCAGCCGCGGCAGCCGCGAGTGGGAGAGGAACCAGAACCTCA | 2350 |
| TCAATGCCTGCACAAAGGACATGCCCCCCATGGGCTCCCCTGTGATTCCC | 2400 |
| ACGGACCTGCCCCTGCGGGCCTCCCCAGCCACATCCCCAGCGTGGTGGT | 2450 |
| CCTGCCCATCACGCAGCAGGGCTACCAGCATGAGTACGTGGACCAGCCCA | 2500 |
| AAATGAGCGAGGTGGCCCAGATGGCGCTGGAGGACCAGGCCGCCACACTG | 2550 |
| GAGTATAAGACCATCAAGGAACATCTCAGCAGCAAGAGTCCCAACCATGG | 2600 |
| GGTGAACCTTGTGGAGAACCTGGACAGCCTGCCCCCAAAGTTCCACAGC | 2650 |
| GGGAGGCCTCCCTGGGTCCCCGGGAGCCTCCCTGTCTCAGACCGGTCTA | 2700 |
| AGCAAGCGGCTGGAAATGCACCACTCCTCTTCCTACGGGGTTGACTATAA | 2750 |
| GAGGAGCTACCCCACGAACTCGCTCACGAGAAGCCACCAGGCCACCACTC | 2800 |
| TCAAAAGAAACAACACTAACTCCTCCAATTCCTCTCACCTCTCCAGAAAC | 2850 |
| CAGAGCTTTGGCAGGGGAGACAACCCGCCGCCCGCCCCGCAGAGGGTGGA | 2900 |
| CTCCATCCAGGTGCACAGCTCCCAGCCATCTGGCCAGGCCGTGACTGTCT | 2950 |
| CGAGGCAGCCCAGCCTCAACGCCTACAACTCACTGACAAGGTCGGGGCTG | 3000 |
| AAGCGTACGCCCTCGCTAAAGCCGGACGTACCCCCCAAACCATCCTTTGC | 3050 |
| TCCCCTTTCCACATCCATGAAGCCCAATGATGCGTGTACATAA-3' | 3093 |

Fig. 2  SEQ ID NO: 6 AND SEQ ID NO: 7

```
ggcacgaggctgcagccaactccgctccccgcgcactcggctgcccaggcgctcgga      57
acccagcagcggcgctcctccgcggtgccggtcgcccgcgatgcccgcttagcagcgtgt   117
agcagcggccagcatcaccacacccgcggcaccgcgctgccggccgcagagccgggccag   177
agccttgccccctccccagcccccaccccgcccccgccctgaaatgacttgttaatc      237
ggcgcagacaccaccaaggggactcaccgaagtggaatccaagtggaatttggatttgga   297
gaagagtttcttgaacatttaccctcttccttgttggttttcttttttcttttctttcttt 357
ttttttttggcttcttttttcctctccccttctccgctcgtcattggagatgaacacatc  417
gcgtttgcatcccagaaagtagtcgccgcgactatttccccaaagagacaagcacacat   477
gtaggaatgacaaaggcttgcgaaggagagagccgcagccgcggcccggagagatcccct   537
cgataatggattactaaatgggatacacgctgtaccagttcgctccgagccccggccgcc  597
tgtccgtcgatgcaccgaaaagggtgaagtagagaaataaagtctccccgctgaactact  657
```

ATGAGGTCAGAAGCCTTGCTGCTATATTTCACACTGCTACACTTTGCTGGGGCTGGTTTC  717
 M  R  S  E  A  L  L  L  Y  F  T  L  L  H  F  A  G  A  G  F
CCAGAAGATTCTGAGCCAATCAGTATTTCGCATGGCAACTATACAAAACAGTATCCGGTG  777
 P  E  D  S  E  P  I  S  I  S  H  G  N  Y  T  K  Q  Y  P  V
TTTGTGGGCCACAAGCCAGGACGGAACACCACACAGAGGCACAGGCTGGACATCCAGATG  837
 F  V  G  H  K  P  G  R  N  T  T  Q  R  H  R  L  D  I  Q  M
ATTATGATCATGAACGGAACCCTCTACATTGCTGCTAGGGACCATATTTATACTGTTGAT  897
 I  M  I  M  N  G  T  L  Y  I  A  A  R  D  H  I  Y  T  V  D
ATAGACACATCACACACGGAAGAAATTTATTGTAGCAAAAAACTGACATGGAAATCTAGA  957
 I  D  T  S  H  T  E  E  I  Y  C  S  K  K  L  T  W  K  S  R
CAGGCCGATGTAGACACATGCAGAATGAAGGGAAAACATAAGGATGAGTGCCACAACTTT 1017
 Q  A  D  V  D  T  C  R  M  K  G  K  H  K  D  E  C  H  N  F
ATTAAAGTTCTTCTAAAGAAAAACGATGATGCATTGTTTGTCTGTGGAACTAATGCCTTC 1077
 I  K  V  L  L  K  K  N  D  D  A  L  F  V  C  G  T  N  A  F
AACCCTTCCTGCAGAAACTATAAGATGGATACATTGGAACCATTCGGGGATGAATTCAGC 1137
 N  P  S  C  R  N  Y  K  M  D  T  L  E  P  F  G  D  E  F  S
GGAATGGCCAGATGCCCATATGATGCCAAACATGCCAACGTTGCACTGTTTGCAGATGGA 1197
 G  M  A  R  C  P  Y  D  A  K  H  A  N  V  A  L  F  A  D  G
AAACTATACTCAGCCACAGTGACTGACTTCCTTGCCATTGACGCAGTCATTTACCGGAGT 1237
 K  L  Y  S  A  T  V  T  D  F  L  A  I  D  A  V  I  Y  R  S
CTTGGAGAAAGCCCTACCCTGCGGACCGTCAAGCACGATTCAAAATGGTTGAAAGAACCA 1297
 L  G  E  S  P  T  L  R  T  V  K  H  D  S  K  W  L  K  E  P
TACTTTGTTCAAGCCGTGGATTACGGAGATTATATCTACTTCTTCTTCAGGGAAATAGCA 1357
 Y  F  V  Q  A  V  D  Y  G  D  Y  I  Y  F  F  F  R  E  I  A
GTGGAGTATAACACCATGGGAAAGGTAGTTTTCCCAAGAGTGGCTCAGGTTTGTAAGAAT 1417
 V  E  Y  N  T  M  G  K  V  V  F  P  R  V  A  Q  V  C  K  N
GATATGGGAGGATCTCAAAGAGTCCTGGAGAAACAGTGGACGTCGTTCCTGAAGGCGCGC 1477
 D  M  G  G  S  Q  R  V  L  E  K  Q  W  T  S  F  L  K  A  R
TTGAACTGCTCAGTTCCTGGAGACTCTCATTTTTATTTCAACATTCTCCAGGCAGTTACA 1537
 L  N  C  S  V  P  G  D  S  H  F  Y  F  N  I  L  Q  A  V  T
GATGTGATTCGTATCAACGGGCGTGATGTTGTCCTGGCAACGTTTTCTACACCTTATAAC 1597
 D  V  I  R  I  N  G  R  D  V  V  L  A  T  F  S  T  P  Y  N
AGCATCCCTGGGTCTGCAGTCTGTGCCTATGACATGCTTGACATTGCCAGTGTTTTTACT 1657
 S  I  P  G  S  A  V  C  A  Y  D  M  L  D  I  A  S  V  F  T

Fig. 2 (cont.)

```
GGGAGATTCAAGGAACAGAAGTCTCCTGATTCCACCTGGACACCAGTTCCTGATGAACGA   1717
 G  R  F  K  E  Q  K  S  P  D  S  T  W  T  P  V  P  D  E  R
GTTCCTAAGCCCAGGCCAGGTTGCTGTGCTGGCTCATCCTCCTTAGAAAGATATGCAACC   1777
 V  P  K  P  R  P  G  C  C  A  G  S  S  S  L  E  R  Y  A  T
TCCAATGAGTTCCCTGATGATACCCTGAACTTCATCAAGACGCACCCGCTCATGGATGAG   1837
 S  N  E  F  P  D  D  T  L  N  F  I  K  T  H  P  L  M  D  E
GCAGTGCCCTCCATCTTCAACAGGCCATGGTTCCTGAGAACAATGGTCAGATACCGCCTT   1897
 A  V  P  S  I  F  N  R  P  W  F  L  R  T  M  V  R  Y  R  L
ACCAAAATTGCAGTGGACACAGCTGCTGGGCCATATCAGAATCACACTGTGGTTTTTCTG   1957
 T  K  I  A  V  D  T  A  A  G  P  Y  Q  N  H  T  V  V  F  L
GGATCAGAGAAGGGAATCATCTTGAAGTTTTTGGCCAGAATAGGAAATAGTGGTTTTCTA   2017
 G  S  E  K  G  I  I  L  K  F  L  A  R  I  G  N  S  G  F  L
AATGACAGCCTTTTCCTGGAGGAGATGAGTGTTTACAACTCTGAAAAATGCAGCTATGAT   2077
 N  D  S  L  F  L  E  E  M  S  V  Y  N  S  E  K  C  S  Y  D
GGAGTCGAAGACAAAAGGATCATGGGCATGCAGCTGGACAGAGCAAGCAGCTCTCTGTAT   2137
 G  V  E  D  K  R  I  M  G  M  Q  L  D  R  A  S  S  S  L  Y
GTTGCGTTCTCTACCTGTGTGATAAAGGTTCCCCTTGGCCGGTGTGAACGACATGGGAAG   2197
 V  A  F  S  T  C  V  I  K  V  P  L  G  R  C  E  R  H  G  K
TGTAAAAAAACCTGTATTGCCTCCAGAGACCCATATTGTGGATGGATAAAGGAAGGTGGT   2257
 C  K  K  T  C  I  A  S  R  D  P  Y  C  G  W  I  K  E  G  G
GCCTGCAGCCATTTATCACCCAACAGCAGACTGACTTTTGAGCAGGACATAGAGCGTGGC   2317
 A  C  S  H  L  S  P  N  S  R  L  T  F  E  Q  D  I  E  R  G
AATACAGATGGTCTGGGGGACTGTCACAATTCCTTTGTGGCACTGAATGGGCATTCCAGT   2377
 N  T  D  G  L  G  D  C  H  N  S  F  V  A  L  N  G  H  S  S
TCCCTCTTGCCCAGCACAACCACATCAGATTCGACGGCTCAAGAGGGGTATGAGTCTAGG   2437
 S  L  L  P  S  T  T  T  S  D  S  T  Q  E  G  Y  E  S  R
GGAGGAATGCTGGACTGGAAGCATCTGCTTGACTCACCTGACAGCACAGACCCTTTGGGG   2497
 G  G  M  L  D  W  K  H  L  L  D  S  P  D  S  T  D  P  L  G
GCAGTGTCTTCCCATAATCACCAAGACAAGAAGGGAGTGATTCGGGAAAGTTACCTCAAA   2557
 A  V  S  S  H  N  H  Q  D  K  K  G  V  I  R  E  S  Y  L  K
GGCCACGACCAGCTGGTTCCCGTCACCCTCTTGGCCATTGCAGTCATCCTGGCTTTCGTC   2617
 G  H  D  Q  L  V  P  V  T  L  L  A  I  A  V  I  L  A  F  V
ATGGGGGCCGTCTTCTCGGGCATCACCGTCTACTGCGTCTGTGATCATCGGCGCAAAGAC   2677
 M  G  A  V  F  S  G  I  T  V  Y  C  V  C  D  H  R  R  K  D
GTGGCTGTGGTGCAGCGCAAGGAGAAGGAGCTCACCCACTCGCGCCGGGGCTCCATGAGC   2737
 V  A  V  V  Q  R  K  E  K  E  L  T  H  S  R  R  G  S  M  S
AGCGTCACCAAGCTCAGCGGCCTCTTTGGGGACACTCAATCCAAAGACCCAAAGCCGGAG   2797
 S  V  T  K  L  S  G  L  F  G  D  T  Q  S  K  D  P  K  P  E
GCCATCCTCACGCCACTCATGCACAACGGCAAGCTCGCCACTCCCGGCAACACGGCCAAG   2857
 A  I  L  T  P  L  M  H  N  G  K  L  A  T  P  G  N  T  A  K
ATGCTCATTAAAGCAGACCAGCACCACCTGGACCTGACGGCCCTCCCCACCCCAGAGTCA   2917
 M  L  I  K  A  D  Q  H  H  L  D  L  T  A  L  P  T  P  E  S
ACCCCAACGCTGCAGCAGAAGCGGAAGCCCAGCCGCGGCAGCCGCGAGTGGGAGAGGAAC   2977
 T  P  T  L  Q  Q  K  R  K  P  S  R  G  S  R  E  W  E  R  N
CAGAACCTCATCAATGCCTGCACAAAGGACATGCCCCCCATGGGCTCCCCTGTGATTCCC   3037
 Q  N  L  I  N  A  C  T  K  D  M  P  P  M  G  S  P  V  I  P
```

Fig. 2 (cont.)

```
ACGGACCTGCCCCTGCGGGCCTCCCCCAGCCACATCCCCAGCGTGGTGGTCCTGCCCATC    3097
 T  D  L  P  L  R  A  S  P  S  H  I  P  S  V  V  V  L  P  I
ACGCAGCAGGGCTACCAGCATGAGTACGTGGACCAGCCCAAAATGAGCGAGGTGGCCCAG    3157
 T  Q  Q  G  Y  Q  H  E  Y  V  D  Q  P  K  M  S  E  V  A  Q
ATGGCGCTGGAGGACCAGGCCGCCACACTGGAGTATAAGACCATCAAGGAACATCTCAGC    3217
 M  A  L  E  D  Q  A  A  T  L  E  Y  K  T  I  K  E  H  L  S
AGCAAGAGTCCCAACCATGGGGTGAACCTTGTGGAGAACCTGGACAGCCTGCCCCCCAAA    3277
 S  K  S  P  N  H  G  V  N  L  V  E  N  L  D  S  L  P  P  K
GTTCCACAGCGGGAGGCCTCCCTGGGTCCCCCGGGAGCCTCCCTGTCTCAGACCGGTCTA    3337
 V  P  Q  R  E  A  S  L  G  P  P  G  A  S  L  S  Q  T  G  L
AGCAAGCGGCTGGAAATGCACCACTCCTCTTCCTACGGGGTTGACTATAAGAGGAGCTAC    3397
 S  K  R  L  E  M  H  H  S  S  S  Y  G  V  D  Y  K  R  S  Y
CCCACGAACTCGCTCACGAGAAGCCACCAGGCCACCACTCTCAAAAGAAACAACACTAAC    3457
 P  T  N  S  L  T  R  S  H  Q  A  T  T  L  K  R  N  N  T  N
TCCTCCAATTCCTCTCACCTCTCCAGAAACCAGAGCTTTGGCAGGGGAGACAACCCGCCG    3517
 S  S  N  S  S  H  L  S  R  N  Q  S  F  G  R  G  D  N  P  P
CCCGCCCCGCAGAGGGTGGACTCCATCCAGGTGCACAGCTCCCAGCCATCTGGCCAGGCC    3577
 P  A  P  Q  R  V  D  S  I  Q  V  H  S  S  Q  P  S  G  Q  A
GTGACTGTCTCGAGGCAGCCCAGCCTCAACGCCTACAACTCACTGACAAGGTCGGGGCTG    3637
 V  T  V  S  R  Q  P  S  L  N  A  Y  N  S  L  T  R  S  G  L
AAGCGTACGCCCTCGCTAAAGCCGGACGTACCCCCCAAACCATCCTTTGCTCCCCTTTCC    3697
 K  R  T  P  S  L  K  P  D  V  P  P  K  P  S  F  A  P  L  S
ACATCCATGAAGCCCAATGATGCGTGTACATAAtccaggggggggggtcaggtgtcga     3757
 T  S  M  K  P  N  D  A  C  T  * accagcaggcaaggcgaggtgcccgctcagctcagcaaggttctcaactgcctcgagtac    3817
ccaccagaccaagaaggcctgcggc
```

(MMU)Sema6A-1 Distribution in Mouse Adult and Embryonic Tissues

Fig. 6

Sequence-Alignment: SEMA6A-1 / Zyxin

```
SEMA6A-1                                                    SEQ ID NO:8   (6a)
PPPAPQRVDSIQVHSSQPSGQAVTVSRQPSLNAYNSLTRSGLKRTPSLKPD-VPPKPSFAPLSTSMKPNDACT
*  *  ***    +*  *   **   +    *   **  +++  *+   *   *   *   *   *+   +     *
PPPQPQRKPQVQLH-VQPQAKP-HVQPQP-VSSANTQPRGPLSQAPTPAPKFAPVAPKFTPVVSKFSP
zyxin                                                       SEQ ID NO:9   (6b)
```

Identity: 33%
Similarity: 49%

A.

| IP:α-Evl | + | + | + |   |   |   |   | |
|---|---|---|---|---|---|---|---|---|
| pFlagCMV-1 | + |   | + |   |   |   | + | |
| pFlagSEMA6A-1 |   | + |   | + | + |   |   | α-Evl |
| SEMA6a-1.purif. |   |   | + |   | + |   |   | |
| HT22 | + | + | + | + | + |   | + | |

SEMA6A-1 →
Evl → kDa
- 250
- 160
- 105
- 75
- 50

B.

| IP:α-Mena | + | + | + |   | |
|---|---|---|---|---|---|
| pFlagCMV-1 | + |   | + |   | α-Mena |
| pFlagSEMA6A-1 |   | + |   | + | |
| SEMA6a-1.purif. |   |   | + |   | |
| HEK | + | + | + | + | |

SEMA6A-1 →
Mena → kDa
- 250
- 160
- 105
- 75
- 50

Fig. 7

From Membrane to Cytoskeleton: Enabling a Connection
(Hu and Reichardt, Neuron, Vol. 22; March 1999)

SEQUENCE LISTING

<160> NUMBER OF SEQ ID NOS: 9

<210> SEQ ID NO 1
<211> LENGTH: 3093
<212> TYPE: DNA
<213> ORGANISM: Homo sapiens
<220> FEATURE:
<221> NAME/KEY: CDS
<222> LOCATION: (1)..(3093)

<400> SEQUENCE: 1

```
atg agg tca gaa gcc ttg ctg cta tat ttc aca ctg cta cac ttt gct      48
Met Arg Ser Glu Ala Leu Leu Leu Tyr Phe Thr Leu Leu His Phe Ala
1               5                   10                  15 ggg gct ggt ttc cca gaa gat tct gag cca atc agt att tcg cat ggc      96
Gly Ala Gly Phe Pro Glu Asp Ser Glu Pro Ile Ser Ile Ser His Gly
                20                  25                  30 aac tat aca aaa cag tat ccg gtg ttt gtg ggc cac aag cca gga cgg     144
Asn Tyr Thr Lys Gln Tyr Pro Val Phe Val Gly His Lys Pro Gly Arg
            35                  40                  45 aac acc aca cag agg cac agg ctg gac atc cag atg att atg atc atg     192
Asn Thr Thr Gln Arg His Arg Leu Asp Ile Gln Met Ile Met Ile Met
        50                  55                  60 aac gga acc ctc tac att gct gct agg gac cat att tat act gtt gat     240
Asn Gly Thr Leu Tyr Ile Ala Ala Arg Asp His Ile Tyr Thr Val Asp
65                  70                  75                  80
```

-continued

```
ata gac aca tca cac acg gaa gaa att tat tgt agc aaa aaa ctg aca      288
Ile Asp Thr Ser His Thr Glu Glu Ile Tyr Cys Ser Lys Lys Leu Thr
                85                  90                  95 tgg aaa tct aga cag gcc gat gta gac aca tgc aga atg aag gga aaa      336
Trp Lys Ser Arg Gln Ala Asp Val Asp Thr Cys Arg Met Lys Gly Lys
        100                 105                 110 cat aag gat gag tgc cac aac ttt att aaa gtt ctt cta aag aaa aac      384
His Lys Asp Glu Cys His Asn Phe Ile Lys Val Leu Leu Lys Lys Asn
            115                 120                 125 gat gat gca ttg ttt gtc tgt gga act aat gcc ttc aac cct tcc tgc      432
Asp Asp Ala Leu Phe Val Cys Gly Thr Asn Ala Phe Asn Pro Ser Cys
130                 135                 140 aga aac tat aag atg gat aca ttg gaa cca ttc ggg gat gaa ttc agc      480
Arg Asn Tyr Lys Met Asp Thr Leu Glu Pro Phe Gly Asp Glu Phe Ser
145                 150                 155                 160 gga atg gcc aga tgc cca tat gat gcc aaa cat gcc aac gtt gca ctg      528
Gly Met Ala Arg Cys Pro Tyr Asp Ala Lys His Ala Asn Val Ala Leu
                165                 170                 175 ttt gca gat gga aaa cta tac tca gcc aca gtg act gac ttc ctt gcc      576
Phe Ala Asp Gly Lys Leu Tyr Ser Ala Thr Val Thr Asp Phe Leu Ala
        180                 185                 190 att gac gca gtc att tac cgg agt ctt gga gaa agc cct acc ctg cgg      624
Ile Asp Ala Val Ile Tyr Arg Ser Leu Gly Glu Ser Pro Thr Leu Arg
            195                 200                 205 acc gtc aag cac gat tca aaa tgg ttg aaa gaa cca tac ttt gtt caa      672
Thr Val Lys His Asp Ser Lys Trp Leu Lys Glu Pro Tyr Phe Val Gln
210                 215                 220 gcc gtg gat tac gga gat tat atc tac ttc ttc ttc agg gaa ata gca      720
Ala Val Asp Tyr Gly Asp Tyr Ile Tyr Phe Phe Phe Arg Glu Ile Ala
225                 230                 235                 240 gtg gag tat aac acc atg gga aag gta gtt ttc cca aga gtg gct cag      768
Val Glu Tyr Asn Thr Met Gly Lys Val Val Phe Pro Arg Val Ala Gln
                245                 250                 255 gtt tgt aag aat gat atg gga gga tct caa aga gtc ctg gag aaa cag      816
Val Cys Lys Asn Asp Met Gly Gly Ser Gln Arg Val Leu Glu Lys Gln
        260                 265                 270 tgg acg tcg ttc ctg aag gcg cgc ttg aac tgc tca gtt cct gga gac      864
Trp Thr Ser Phe Leu Lys Ala Arg Leu Asn Cys Ser Val Pro Gly Asp
            275                 280                 285 tct cat ttt tat ttc aac att ctc cag gca gtt aca gat gtg att cgt      912
Ser His Phe Tyr Phe Asn Ile Leu Gln Ala Val Thr Asp Val Ile Arg
290                 295                 300 atc aac ggg cgt gat gtt gtc ctg gca acg ttt tct aca cct tat aac      960
Ile Asn Gly Arg Asp Val Val Leu Ala Thr Phe Ser Thr Pro Tyr Asn
305                 310                 315                 320 agc atc cct ggg tct gca gtc tgt gcc tat gac atg ctt gac att gcc     1008
Ser Ile Pro Gly Ser Ala Val Cys Ala Tyr Asp Met Leu Asp Ile Ala
                325                 330                 335 agt gtt ttt act ggg aga ttc aag gaa cag aag tct cct gat tcc acc     1056
Ser Val Phe Thr Gly Arg Phe Lys Glu Gln Lys Ser Pro Asp Ser Thr
        340                 345                 350 tgg aca cca gtt cct gat gaa cga gtt cct aag ccc agg cca ggt tgc     1104
Trp Thr Pro Val Pro Asp Glu Arg Val Pro Lys Pro Arg Pro Gly Cys
            355                 360                 365 tgt gct ggc tca tcc tcc tta gaa aga tat gca acc tcc aat gag ttc     1152
Cys Ala Gly Ser Ser Ser Leu Glu Arg Tyr Ala Thr Ser Asn Glu Phe
370                 375                 380 cct gat gat acc ctg aac ttc atc aag acg cac ccg ctc atg gat gag     1200
Pro Asp Asp Thr Leu Asn Phe Ile Lys Thr His Pro Leu Met Asp Glu
```

-continued

| | | | | | | | | | | | | | | | |
|---|---|---|---|---|---|---|---|---|---|---|---|---|---|---|---|
| 385 | | | | 390 | | | | 395 | | | | 400 | | | |
| gca | gtg | ccc | tcc | atc | ttc | aac | agg | cca | tgg | ttc | ctg | aga | aca | atg | gtc | 1248 |
| Ala | Val | Pro | Ser | Ile | Phe | Asn | Arg | Pro | Trp | Phe | Leu | Arg | Thr | Met | Val | |
| | | | | 405 | | | | | 410 | | | | | 415 | | |
| aga | tac | cgc | ctt | acc | aaa | att | gca | gtg | gac | aca | gct | gct | ggg | cca | tat | 1296 |
| Arg | Tyr | Arg | Leu | Thr | Lys | Ile | Ala | Val | Asp | Thr | Ala | Ala | Gly | Pro | Tyr | |
| | | | 420 | | | | | 425 | | | | | 430 | | | |
| cag | aat | cac | act | gtg | gtt | ttt | ctg | gga | tca | gag | aag | gga | atc | atc | ttg | 1344 |
| Gln | Asn | His | Thr | Val | Val | Phe | Leu | Gly | Ser | Glu | Lys | Gly | Ile | Ile | Leu | |
| | | | 435 | | | | | 440 | | | | | 445 | | | |
| aag | ttt | ttg | gcc | aga | ata | gga | aat | agt | ggt | ttt | cta | aat | gac | agc | ctt | 1392 |
| Lys | Phe | Leu | Ala | Arg | Ile | Gly | Asn | Ser | Gly | Phe | Leu | Asn | Asp | Ser | Leu | |
| | 450 | | | | | 455 | | | | | 460 | | | | | |
| ttc | ctg | gag | gag | atg | agt | gtt | tac | aac | tct | gaa | aaa | tgc | agc | tat | gat | 1440 |
| Phe | Leu | Glu | Glu | Met | Ser | Val | Tyr | Asn | Ser | Glu | Lys | Cys | Ser | Tyr | Asp | |
| 465 | | | | | 470 | | | | | 475 | | | | | 480 | |
| gga | gtc | gaa | gac | aaa | agg | atc | atg | ggc | atg | cag | ctg | gac | aga | gca | agc | 1488 |
| Gly | Val | Glu | Asp | Lys | Arg | Ile | Met | Gly | Met | Gln | Leu | Asp | Arg | Ala | Ser | |
| | | | | 485 | | | | | 490 | | | | | 495 | | |
| agc | tct | ctg | tat | gtt | gcg | ttc | tct | acc | tgt | gtg | ata | aag | gtt | ccc | ctt | 1536 |
| Ser | Ser | Leu | Tyr | Val | Ala | Phe | Ser | Thr | Cys | Val | Ile | Lys | Val | Pro | Leu | |
| | | | 500 | | | | | 505 | | | | | 510 | | | |
| ggc | cgg | tgt | gaa | cga | cat | ggg | aag | tgt | aaa | aaa | acc | tgt | att | gcc | tcc | 1584 |
| Gly | Arg | Cys | Glu | Arg | His | Gly | Lys | Cys | Lys | Lys | Thr | Cys | Ile | Ala | Ser | |
| | | | 515 | | | | | 520 | | | | | 525 | | | |
| aga | gac | cca | tat | tgt | gga | tgg | ata | aag | gaa | ggt | ggt | gcc | tgc | agc | cat | 1632 |
| Arg | Asp | Pro | Tyr | Cys | Gly | Trp | Ile | Lys | Glu | Gly | Gly | Ala | Cys | Ser | His | |
| | 530 | | | | | 535 | | | | | 540 | | | | | |
| tta | tca | ccc | aac | agc | aga | ctg | act | ttt | gag | cag | gac | ata | gag | cgt | ggc | 1680 |
| Leu | Ser | Pro | Asn | Ser | Arg | Leu | Thr | Phe | Glu | Gln | Asp | Ile | Glu | Arg | Gly | |
| 545 | | | | | 550 | | | | | 555 | | | | | 560 | |
| aat | aca | gat | ggt | ctg | ggg | gac | tgt | cac | aat | tcc | ttt | gtg | gca | ctg | aat | 1728 |
| Asn | Thr | Asp | Gly | Leu | Gly | Asp | Cys | His | Asn | Ser | Phe | Val | Ala | Leu | Asn | |
| | | | | 565 | | | | | 570 | | | | | 575 | | |
| ggg | cat | tcc | agt | tcc | ctc | ttg | ccc | agc | aca | acc | aca | tca | gat | tcg | acg | 1776 |
| Gly | His | Ser | Ser | Leu | Leu | Pro | Ser | Thr | Thr | Thr | Ser | Asp | Ser | Thr | |
| | | | 580 | | | | | 585 | | | | | 590 | | | |
| gct | caa | gag | ggg | tat | gag | tct | agg | gga | gga | atg | ctg | gac | tgg | aag | cat | 1824 |
| Ala | Gln | Glu | Gly | Tyr | Glu | Ser | Arg | Gly | Gly | Met | Leu | Asp | Trp | Lys | His | |
| | | | 595 | | | | | 600 | | | | | 605 | | | |
| ctg | ctt | gac | tca | cct | gac | agc | aca | gac | cct | ttg | ggg | gca | gtg | tct | tcc | 1872 |
| Leu | Leu | Asp | Ser | Pro | Asp | Ser | Thr | Asp | Pro | Leu | Gly | Ala | Val | Ser | Ser | |
| | 610 | | | | | 615 | | | | | 620 | | | | | |
| cat | aat | cac | caa | gac | aag | aag | gga | gtg | att | cgg | gaa | agt | tac | ctc | aaa | 1920 |
| His | Asn | His | Gln | Asp | Lys | Lys | Gly | Val | Ile | Arg | Glu | Ser | Tyr | Leu | Lys | |
| 625 | | | | | 630 | | | | | 635 | | | | | 640 | |
| ggc | cac | gac | cag | ctg | gtt | ccc | gtc | acc | ctc | ttg | gcc | att | gca | gtc | atc | 1968 |
| Gly | His | Asp | Gln | Leu | Val | Pro | Val | Thr | Leu | Leu | Ala | Ile | Ala | Val | Ile | |
| | | | | 645 | | | | | 650 | | | | | 655 | | |
| ctg | gct | ttc | gtc | atg | ggg | gcc | gtc | ttc | tcg | ggc | atc | acc | gtc | tac | tgc | 2016 |
| Leu | Ala | Phe | Val | Met | Gly | Ala | Val | Phe | Ser | Gly | Ile | Thr | Val | Tyr | Cys | |
| | | | 660 | | | | | 665 | | | | | 670 | | | |
| gtc | tgt | gat | cat | cgg | cgc | aaa | gac | gtg | gct | gtg | gtg | cag | cgc | aag | gag | 2064 |
| Val | Cys | Asp | His | Arg | Arg | Lys | Asp | Val | Ala | Val | Val | Gln | Arg | Lys | Glu | |
| | | | 675 | | | | | 680 | | | | | 685 | | | |
| aag | gag | ctc | acc | cac | tcg | cgc | cgg | ggc | tcc | atg | agc | agc | gtc | acc | aag | 2112 |
| Lys | Glu | Leu | Thr | His | Ser | Arg | Arg | Gly | Ser | Met | Ser | Ser | Val | Thr | Lys | |
| | 690 | | | | | 695 | | | | | 700 | | | | | |
| ctc | agc | ggc | ctc | ttt | ggg | gac | act | caa | tcc | aaa | gac | cca | aag | ccg | gag | 2160 |

|   |   |
|---|---|
| Leu Ser Gly Leu Phe Gly Asp Thr Gln Ser Lys Asp Pro Lys Pro Glu<br>705                 710                 715                 720 |   |
| gcc atc ctc acg cca ctc atg cac aac ggc aag ctc gcc act ccc ggc<br>Ala Ile Leu Thr Pro Leu Met His Asn Gly Lys Leu Ala Thr Pro Gly<br>            725                 730                 735 | 2208 |
| aac acg gcc aag atg ctc att aaa gca gac cag cac cac ctg gac ctg<br>Asn Thr Ala Lys Met Leu Ile Lys Ala Asp Gln His His Leu Asp Leu<br>740                 745                 750 | 2256 |
| acg gcc ctc ccc acc cca gag tca acc cca acg ctg cag cag aag cgg<br>Thr Ala Leu Pro Thr Pro Glu Ser Thr Pro Thr Leu Gln Gln Lys Arg<br>            755                 760                 765 | 2304 |
| aag ccc agc cgc ggc agc cgc gag tgg gag agg aac cag aac ctc atc<br>Lys Pro Ser Arg Gly Ser Arg Glu Trp Glu Arg Asn Gln Asn Leu Ile<br>770                 775                 780 | 2352 |
| aat gcc tgc aca aag gac atg ccc ccc atg ggc tcc cct gtg att ccc<br>Asn Ala Cys Thr Lys Asp Met Pro Pro Met Gly Ser Pro Val Ile Pro<br>785                 790                 795                 800 | 2400 |
| acg gac ctg ccc ctg cgg gcc tcc ccc agc cac atc ccc agc gtg gtg<br>Thr Asp Leu Pro Leu Arg Ala Ser Pro Ser His Ile Pro Ser Val Val<br>            805                 810                 815 | 2448 |
| gtc ctg ccc atc acg cag cag ggc tac cag cat gag tac gtg gac cag<br>Val Leu Pro Ile Thr Gln Gln Gly Tyr Gln His Glu Tyr Val Asp Gln<br>820                 825                 830 | 2496 |
| ccc aaa atg agc gag gtg gcc cag atg gcg ctg gag gac cag gcc gcc<br>Pro Lys Met Ser Glu Val Ala Gln Met Ala Leu Glu Asp Gln Ala Ala<br>            835                 840                 845 | 2544 |
| aca ctg gag tat aag acc atc aag gaa cat ctc agc agc aag agt ccc<br>Thr Leu Glu Tyr Lys Thr Ile Lys Glu His Leu Ser Ser Lys Ser Pro<br>850                 855                 860 | 2592 |
| aac cat ggg gtg aac ctt gtg gag aac ctg gac agc ctg ccc ccc aaa<br>Asn His Gly Val Asn Leu Val Glu Asn Leu Asp Ser Leu Pro Pro Lys<br>865                 870                 875                 880 | 2640 |
| gtt cca cag cgg gag gcc tcc ctg ggt ccc ccg gga gcc tcc ctg tct<br>Val Pro Gln Arg Glu Ala Ser Leu Gly Pro Pro Gly Ala Ser Leu Ser<br>            885                 890                 895 | 2688 |
| cag acc ggt cta agc aag cgg ctg gaa atg cac cac tcc tct tcc tac<br>Gln Thr Gly Leu Ser Lys Arg Leu Glu Met His His Ser Ser Ser Tyr<br>900                 905                 910 | 2736 |
| ggg gtt gac tat aag agg agc tac ccc acg aac tcg ctc acg aga agc<br>Gly Val Asp Tyr Lys Arg Ser Tyr Pro Thr Asn Ser Leu Thr Arg Ser<br>            915                 920                 925 | 2784 |
| cac cag gcc acc act ctc aaa aga aac aac act aac tcc tcc aat tcc<br>His Gln Ala Thr Thr Leu Lys Arg Asn Asn Thr Asn Ser Ser Asn Ser<br>930                 935                 940 | 2832 |
| tct cac ctc tcc aga aac cag agc ttt ggc agg gga gac aac ccg ccg<br>Ser His Leu Ser Arg Asn Gln Ser Phe Gly Arg Gly Asp Asn Pro Pro<br>945                 950                 955                 960 | 2880 |
| ccc gcc ccg cag agg gtg gac tcc atc cag gtg cac agc tcc cag cca<br>Pro Ala Pro Gln Arg Val Asp Ser Ile Gln Val His Ser Ser Gln Pro<br>            965                 970                 975 | 2928 |
| tct ggc cag gcc gtg act gtc tcg agg cag ccc agc ctc aac gcc tac<br>Ser Gly Gln Ala Val Thr Val Ser Arg Gln Pro Ser Leu Asn Ala Tyr<br>980                 985                 990 | 2976 |
| aac tca ctg aca agg tcg ggg ctg  aag cgt acg ccc tcg  cta aag ccg<br>Asn Ser Leu Thr Arg Ser Gly Leu  Lys Arg Thr Pro Ser  Leu Lys Pro<br>            995                 1000                1005 | 3024 |
| gac gta  ccc ccc aaa cca tcc  ttt gct ccc ctt tcc  aca tcc atg<br>Asp Val  Pro Pro Lys Pro Ser  Phe Ala Pro Leu Ser  Thr Ser Met<br>    1010                1015                1020 | 3069 |

```
aag ccc aat gat gcg tgt aca taa                                                    3093
Lys Pro Asn Asp Ala Cys Thr
    1025                1030
```

<210> SEQ ID NO 2
<211> LENGTH: 1030
<212> TYPE: PRT
<213> ORGANISM: Homo sapiens

<400> SEQUENCE: 2

```
Met Arg Ser Glu Ala Leu Leu Tyr Phe Thr Leu His Phe Ala
1               5                   10                  15

Gly Ala Gly Phe Pro Glu Asp Ser Glu Pro Ile Ser Ile Ser His Gly
                20                  25                  30

Asn Tyr Thr Lys Gln Tyr Pro Val Phe Val Gly His Lys Pro Gly Arg
            35                  40                  45

Asn Thr Thr Gln Arg His Arg Leu Asp Ile Gln Met Ile Met Ile Met
50                  55                  60

Asn Gly Thr Leu Tyr Ile Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
                100                 105                 110

His Lys Asp Glu Cys His Asn Phe Ile Lys Val Leu Leu Lys Lys Asn
            115                 120                 125

Asp Asp Ala Leu Phe Val Cys Gly Thr Asn Ala Phe Asn Pro Ser Cys
130                 135                 140

Arg Asn Tyr Lys Met Asp Thr Leu Glu Pro Phe Gly Asp Glu Phe Ser
145                 150                 155                 160

Gly Met Ala Arg Cys Pro Tyr Asp Ala Lys His Ala Asn Val Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Glu Ser Pro Thr Leu Arg
            195                 200                 205

Thr Val Lys His Asp Ser Lys Trp Leu Lys Glu Pro Tyr Phe Val Gln
210                 215                 220

Ala Val Asp Tyr Gly Asp Tyr Ile Tyr Phe Phe Arg Glu Ile Ala
225                 230                 235                 240

Val Glu Tyr Asn Thr Met Gly Lys Val Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
            275                 280                 285

Ser His Phe Tyr Phe Asn Ile Leu Gln Ala Val Thr Asp Val Ile Arg
290                 295                 300

Ile Asn Gly Arg Asp Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                325                 330                 335

Ser Val Phe Thr Gly Arg Phe Lys Glu Gln Lys Ser Pro Asp Ser Thr
            340                 345                 350

Trp Thr Pro Val Pro Asp Glu Arg Val Pro Lys Pro Arg Pro Gly Cys
```

-continued

```
            355                 360                 365
Cys Ala Gly Ser Ser Ser Leu Glu Arg Tyr Ala Thr Ser Asn Glu Phe
    370                 375                 380
Pro Asp Asp Thr Leu Asn Phe Ile Lys Thr His Pro Leu Met Asp Glu
385                 390                 395                 400
Ala Val Pro Ser Ile Phe Asn Arg Pro Trp Phe Leu Arg Thr Met Val
                405                 410                 415
Arg Tyr Arg Leu Thr Lys Ile Ala Val Asp Thr Ala Ala Gly Pro Tyr
            420                 425                 430
Gln Asn His Thr Val Val Phe Leu Gly Ser Glu Lys Gly Ile Ile Leu
        435                 440                 445
Lys Phe Leu Ala Arg Ile Gly Asn Ser Gly Phe Leu Asn Asp Ser Leu
450                 455                 460
Phe Leu Glu Glu Met Ser Val Tyr Asn Ser Glu Lys Cys Ser Tyr Asp
465                 470                 475                 480
Gly Val Glu Asp Lys Arg Ile Met Gly Met Gln Leu Asp Arg Ala Ser
                485                 490                 495
Ser Ser Leu Tyr Val Ala Phe Ser Thr Cys Val Ile Lys Val Pro Leu
            500                 505                 510
Gly Arg Cys Glu Arg His Gly Lys Cys Lys Lys Thr Cys Ile Ala Ser
        515                 520                 525
Arg Asp Pro Tyr Cys Gly Trp Ile Lys Glu Gly Gly Ala Cys Ser His
530                 535                 540
Leu Ser Pro Asn Ser Arg Leu Thr Phe Glu Gln Asp Ile Glu Arg Gly
545                 550                 555                 560
Asn Thr Asp Gly Leu Gly Asp Cys His Asn Ser Phe Val Ala Leu Asn
                565                 570                 575
Gly His Ser Ser Leu Leu Pro Ser Thr Thr Ser Asp Ser Thr
            580                 585                 590
Ala Gln Glu Gly Tyr Glu Ser Arg Gly Gly Met Leu Asp Trp Lys His
        595                 600                 605
Leu Leu Asp Ser Pro Asp Ser Thr Asp Pro Leu Gly Ala Val Ser Ser
610                 615                 620
His Asn His Gln Asp Lys Lys Gly Val Ile Arg Glu Ser Tyr Leu Lys
625                 630                 635                 640
Gly His Asp Gln Leu Val Pro Val Thr Leu Leu Ala Ile Ala Val Ile
                645                 650                 655
Leu Ala Phe Val Met Gly Ala Val Phe Ser Gly Ile Thr Val Tyr Cys
            660                 665                 670
Val Cys Asp His Arg Arg Lys Asp Val Ala Val Gln Arg Lys Glu
        675                 680                 685
Lys Glu Leu Thr His Ser Arg Arg Gly Ser Met Ser Ser Val Thr Lys
        690                 695                 700
Leu Ser Gly Leu Phe Gly Asp Thr Gln Ser Lys Asp Pro Lys Pro Glu
705                 710                 715                 720
Ala Ile Leu Thr Pro Leu Met His Asn Gly Lys Leu Ala Thr Pro Gly
                725                 730                 735
Asn Thr Ala Lys Met Leu Ile Lys Ala Asp Gln His His Leu Asp Leu
            740                 745                 750
Thr Ala Leu Pro Thr Pro Glu Ser Thr Pro Thr Leu Gln Gln Lys Arg
        755                 760                 765
Lys Pro Ser Arg Gly Ser Arg Glu Trp Glu Arg Asn Gln Asn Leu Ile
770                 775                 780
```

-continued

```
Asn Ala Cys Thr Lys Asp Met Pro Pro Met Gly Ser Pro Val Ile Pro
785                 790                 795                 800

Thr Asp Leu Pro Leu Arg Ala Ser Pro Ser His Ile Pro Ser Val Val
            805                 810                 815

Val Leu Pro Ile Thr Gln Gln Gly Tyr Gln His Glu Tyr Val Asp Gln
        820                 825                 830

Pro Lys Met Ser Glu Val Ala Gln Met Ala Leu Glu Asp Gln Ala Ala
    835                 840                 845

Thr Leu Glu Tyr Lys Thr Ile Lys Glu His Leu Ser Ser Lys Ser Pro
850                 855                 860

Asn His Gly Val Asn Leu Val Glu Asn Leu Asp Ser Leu Pro Pro Lys
865                 870                 875                 880

Val Pro Gln Arg Glu Ala Ser Leu Gly Pro Pro Gly Ala Ser Leu Ser
            885                 890                 895

Gln Thr Gly Leu Ser Lys Arg Leu Glu Met His His Ser Ser Ser Tyr
        900                 905                 910

Gly Val Asp Tyr Lys Arg Ser Tyr Pro Thr Asn Ser Leu Thr Arg Ser
    915                 920                 925

His Gln Ala Thr Thr Leu Lys Arg Asn Asn Thr Asn Ser Ser Asn Ser
930                 935                 940

Ser His Leu Ser Arg Asn Gln Ser Phe Gly Arg Gly Asp Asn Pro Pro
945                 950                 955                 960

Pro Ala Pro Gln Arg Val Asp Ser Ile Gln Val His Ser Ser Gln Pro
            965                 970                 975

Ser Gly Gln Ala Val Thr Val Ser Arg Gln Pro Ser Leu Asn Ala Tyr
        980                 985                 990

Asn Ser Leu Thr Arg Ser Gly Leu Lys Arg Thr Pro Ser Leu Lys Pro
    995                 1000                1005

Asp Val Pro Pro Lys Pro Ser Phe Ala Pro Leu Ser Thr Ser Met
    1010                1015                1020

Lys Pro Asn Asp Ala Cys Thr
    1025                1030

<210> SEQ ID NO 3
<211> LENGTH: 216
<212> TYPE: DNA
<213> ORGANISM: Homo sapiens
<220> FEATURE:
<221> NAME/KEY: CDS
<222> LOCATION: (1)..(216)

<400> SEQUENCE: 3 ccg ccg ccc gcc ccg cag agg gtg gac tcc atc cag gtg cac agc tcc      48
Pro Pro Pro Ala Pro Gln Arg Val Asp Ser Ile Gln Val His Ser Ser
1               5                   10                  15 cag cca tct ggc cag gcc gtg act gtc tcg agg cag ccc agc ctc aac      96
Gln Pro Ser Gly Gln Ala Val Thr Val Ser Arg Gln Pro Ser Leu Asn
                20                  25                  30 gcc tac aac tca ctg aca agg tcg ggg ctg aag cgt acg ccc tcg cta     144
Ala Tyr Asn Ser Leu Thr Arg Ser Gly Leu Lys Arg Thr Pro Ser Leu
            35                  40                  45 aag ccg gac gta ccc ccc aaa cca tcc ttt gct ccc ctt tcc aca tcc     192
Lys Pro Asp Val Pro Pro Lys Pro Ser Phe Ala Pro Leu Ser Thr Ser
        50                  55                  60 atg aag ccc aat gat gcg tgt aca                                     216
Met Lys Pro Asn Asp Ala Cys Thr
65                  70
```

<210> SEQ ID NO 4
<211> LENGTH: 72
<212> TYPE: PRT
<213> ORGANISM: Homo sapiens

<400> SEQUENCE: 4

```
Pro Pro Pro Ala Pro Gln Arg Val Asp Ser Ile Gln Val His Ser Ser
 1               5                  10                  15

Gln Pro Ser Gly Gln Ala Val Thr Val Ser Arg Gln Pro Ser Leu Asn
            20                  25                  30

Ala Tyr Asn Ser Leu Thr Arg Ser Gly Leu Lys Arg Thr Pro Ser Leu
        35                  40                  45

Lys Pro Asp Val Pro Lys Pro Ser Phe Ala Pro Leu Ser Thr Ser
    50                  55                  60

Met Lys Pro Asn Asp Ala Cys Thr
65                  70
```

<210> SEQ ID NO 5
<211> LENGTH: 65
<212> TYPE: PRT
<213> ORGANISM: Homo sapiens

<400> SEQUENCE: 5

```
Pro Pro Pro Gln Pro Gln Arg Lys Pro Gln Val Gln Leu His Val Gln
 1               5                  10                  15

Pro Gln Ala Lys Pro His Val Gln Pro Gln Pro Val Ser Ser Ala Asn
            20                  25                  30

Thr Gln Pro Arg Gly Pro Leu Ser Gln Ala Pro Thr Pro Ala Pro Lys
        35                  40                  45

Phe Ala Pro Val Ala Pro Lys Phe Thr Pro Val Val Ser Lys Phe Ser
    50                  55                  60

Pro
65
```

<210> SEQ ID NO 6
<211> LENGTH: 3862
<212> TYPE: DNA
<213> ORGANISM: Homo sapiens
<220> FEATURE:
<221> NAME/KEY: CDS
<222> LOCATION: (658)..(3750)

<400> SEQUENCE: 6

| | |
|---|---|
| ggcacgaggc tgcagccaac tccgctcccc gcgcactcgg ctgcccaggc gctcggaacc | 60 |
| cagcagcggc gctcctccgc ggtgccggtc gcccgcgatg cccgcttagc agcgtgtagc | 120 |
| agcggccagc atcaccacac ccgcggcacc gcgctgccgg ccgcagagcc gggccagagc | 180 |
| cttgcccccc tccccagcc cccaccccgc ccccgccct gaaatgactt gttaatcggc | 240 |
| gcagacacca ccaaggggac tcaccgaagt ggaatccaag tggaatttgg atttggagaa | 300 |
| gagtttcttg aacatttacc ctcttccttg ttggttttct ttttcttttt cttcttttt | 360 |
| tttttggctt cttttttcct ctccccttct ccgctcgtca ttggagatga acacatcgcg | 420 |
| tttgcatccc agaaagtagt cgccgcgact atttccccca aagagacaag cacacatgta | 480 |
| ggaatgacaa aggcttgcga aggagagagc cgcagccgcg gcccggagag atcccctcga | 540 |
| taatggatta ctaaatggga tacacgctgt accagttcgc tccgagcccc ggccgcctgt | 600 |
| ccgtcgatgc accgaaaagg gtgaagtaga gaaataaagt ctccccgctg aactact | 657 |

-continued

| | | |
|---|---|---|
| atg agg tca gaa gcc ttg ctg cta tat ttc aca ctg cta cac ttt gct<br>Met Arg Ser Glu Ala Leu Leu Leu Tyr Phe Thr Leu Leu His Phe Ala<br>1               5                   10                  15 | | 705 |
| ggg gct ggt ttc cca gaa gat tct gag cca atc agt att tcg cat ggc<br>Gly Ala Gly Phe Pro Glu Asp Ser Glu Pro Ile Ser Ile Ser His Gly<br>        20                  25                  30 | | 753 |
| aac tat aca aaa cag tat ccg gtg ttt gtg ggc cac aag cca gga cgg<br>Asn Tyr Thr Lys Gln Tyr Pro Val Phe Val Gly His Lys Pro Gly Arg<br>    35                  40                  45 | | 801 |
| aac acc aca cag agg cac agg ctg gac atc cag atg att atg atc atg<br>Asn Thr Thr Gln Arg His Arg Leu Asp Ile Gln Met Ile Met Ile Met<br>50                  55                  60 | | 849 |
| aac gga acc ctc tac att gct gct agg gac cat att tat act gtt gat<br>Asn Gly Thr Leu Tyr Ile Ala Ala Arg Asp His Ile Tyr Thr Val Asp<br>65                  70                  75                  80 | | 897 |
| ata gac aca tca cac acg gaa gaa att tat tgt agc aaa aaa ctg aca<br>Ile Asp Thr Ser His Thr Glu Glu Ile Tyr Cys Ser Lys Lys Leu Thr<br>                85                  90                  95 | | 945 |
| tgg aaa tct aga cag gcc gat gta gac aca tgc aga atg aag gga aaa<br>Trp Lys Ser Arg Gln Ala Asp Val Asp Thr Cys Arg Met Lys Gly Lys<br>            100                 105                 110 | | 993 |
| cat aag gat gag tgc cac aac ttt att aaa gtt ctt cta aag aaa aac<br>His Lys Asp Glu Cys His Asn Phe Ile Lys Val Leu Leu Lys Lys Asn<br>        115                 120                 125 | | 1041 |
| gat gat gca ttg ttt gtc tgt gga act aat gcc ttc aac cct tcc tgc<br>Asp Asp Ala Leu Phe Val Cys Gly Thr Asn Ala Phe Asn Pro Ser Cys<br>    130                 135                 140 | | 1089 |
| aga aac tat aag atg gat aca ttg gaa cca ttc ggg gat gaa ttc agc<br>Arg Asn Tyr Lys Met Asp Thr Leu Glu Pro Phe Gly Asp Glu Phe Ser<br>145                 150                 155                 160 | | 1137 |
| gga atg gcc aga tgc cca tat gat gcc aaa cat gcc aac gtt gca ctg<br>Gly Met Ala Arg Cys Pro Tyr Asp Ala Lys His Ala Asn Val Ala Leu<br>                165                 170                 175 | | 1185 |
| ttt gca gat gga aaa cta tac tca gcc aca gtg act gac ttc ctt gcc<br>Phe Ala Asp Gly Lys Leu Tyr Ser Ala Thr Val Thr Asp Phe Leu Ala<br>            180                 185                 190 | | 1233 |
| att gac gca gtc att tac cgg agt ctt gga gaa agc cct acc ctg cgg<br>Ile Asp Ala Val Ile Tyr Arg Ser Leu Gly Glu Ser Pro Thr Leu Arg<br>        195                 200                 205 | | 1281 |
| acc gtc aag cac gat tca aaa tgg ttg aaa gaa cca tac ttt gtt caa<br>Thr Val Lys His Asp Ser Lys Trp Leu Lys Glu Pro Tyr Phe Val Gln<br>    210                 215                 220 | | 1329 |
| gcc gtg gat tac gga gat tat atc tac ttc ttc ttc agg gaa ata gca<br>Ala Val Asp Tyr Gly Asp Tyr Ile Tyr Phe Phe Phe Arg Glu Ile Ala<br>225                 230                 235                 240 | | 1377 |
| gtg gag tat aac acc atg gga aag gta gtt ttc cca aga gtg gct cag<br>Val Glu Tyr Asn Thr Met Gly Lys Val Val Phe Pro Arg Val Ala Gln<br>                245                 250                 255 | | 1425 |
| gtt tgt aag aat gat atg gga gga tct caa aga gtc ctg gag aaa cag<br>Val Cys Lys Asn Asp Met Gly Gly Ser Gln Arg Val Leu Glu Lys Gln<br>            260                 265                 270 | | 1473 |
| tgg acg tcg ttc ctg aag gcg cgc ttg aac tgc tca gtt cct gga gac<br>Trp Thr Ser Phe Leu Lys Ala Arg Leu Asn Cys Ser Val Pro Gly Asp<br>        275                 280                 285 | | 1521 |
| tct cat ttt tat ttc aac att ctc cag gca gtt aca gat gtg att cgt<br>Ser His Phe Tyr Phe Asn Ile Leu Gln Ala Val Thr Asp Val Ile Arg<br>    290                 295                 300 | | 1569 |
| atc aac ggg cgt gat gtt gtc ctg gca acg ttt tct aca cct tat aac<br>Ile Asn Gly Arg Asp Val Val Leu Ala Thr Phe Ser Thr Pro Tyr Asn<br>305                 310                 315                 320 | | 1617 |

-continued

| | |
|---|---|
| agc atc cct ggg tct gca gtc tgt gcc tat gac atg ctt gac att gcc<br>Ser Ile Pro Gly Ser Ala Val Cys Ala Tyr Asp Met Leu Asp Ile Ala<br>325 330 335 | 1665 |
| agt gtt ttt act ggg aga ttc aag gaa cag aag tct cct gat tcc acc<br>Ser Val Phe Thr Gly Arg Phe Lys Glu Gln Lys Ser Pro Asp Ser Thr<br>340 345 350 | 1713 |
| tgg aca cca gtt cct gat gaa cga gtt cct aag ccc agg cca ggt tgc<br>Trp Thr Pro Val Pro Asp Glu Arg Val Pro Lys Pro Arg Pro Gly Cys<br>355 360 365 | 1761 |
| tgt gct ggc tca tcc tcc tta gaa aga tat gca acc tcc aat gag ttc<br>Cys Ala Gly Ser Ser Ser Leu Glu Arg Tyr Ala Thr Ser Asn Glu Phe<br>370 375 380 | 1809 |
| cct gat gat acc ctg aac ttc atc aag acg cac ccg ctc atg gat gag<br>Pro Asp Asp Thr Leu Asn Phe Ile Lys Thr His Pro Leu Met Asp Glu<br>385 390 395 400 | 1857 |
| gca gtg ccc tcc atc ttc aac agg cca tgg ttc ctg aga aca atg gtc<br>Ala Val Pro Ser Ile Phe Asn Arg Pro Trp Phe Leu Arg Thr Met Val<br>405 410 415 | 1905 |
| aga tac cgc ctt acc aaa att gca gtg gac aca gct gct ggg cca tat<br>Arg Tyr Arg Leu Thr Lys Ile Ala Val Asp Thr Ala Ala Gly Pro Tyr<br>420 425 430 | 1953 |
| cag aat cac act gtg gtt ttt ctg gga tca gag aag gga atc atc ttg<br>Gln Asn His Thr Val Val Phe Leu Gly Ser Glu Lys Gly Ile Ile Leu<br>435 440 445 | 2001 |
| aag ttt ttg gcc aga ata gga aat agt ggt ttt cta aat gac agc ctt<br>Lys Phe Leu Ala Arg Ile Gly Asn Ser Gly Phe Leu Asn Asp Ser Leu<br>450 455 460 | 2049 |
| ttc ctg gag gag atg agt gtt tac aac tct gaa aaa tgc agc tat gat<br>Phe Leu Glu Glu Met Ser Val Tyr Asn Ser Glu Lys Cys Ser Tyr Asp<br>465 470 475 480 | 2097 |
| gga gtc gaa gac aaa agg atc atg ggc atg cag ctg gac aga gca agc<br>Gly Val Glu Asp Lys Arg Ile Met Gly Met Gln Leu Asp Arg Ala Ser<br>485 490 495 | 2145 |
| agc tct ctg tat gtt gcg ttc tct acc tgt gtg ata aag gtt ccc ctt<br>Ser Ser Leu Tyr Val Ala Phe Ser Thr Cys Val Ile Lys Val Pro Leu<br>500 505 510 | 2193 |
| ggc cgg tgt gaa cga cat ggg aag tgt aaa aaa acc tgt att gcc tcc<br>Gly Arg Cys Glu Arg His Gly Lys Cys Lys Lys Thr Cys Ile Ala Ser<br>515 520 525 | 2241 |
| aga gac cca tat tgt gga tgg ata aag gaa ggt ggt gcc tgc agc cat<br>Arg Asp Pro Tyr Cys Gly Trp Ile Lys Glu Gly Gly Ala Cys Ser His<br>530 535 540 | 2289 |
| tta tca ccc aac agc aga ctg act ttt gag cag gac ata gag cgt ggc<br>Leu Ser Pro Asn Ser Arg Leu Thr Phe Glu Gln Asp Ile Glu Arg Gly<br>545 550 555 560 | 2337 |
| aat aca gat ggt ctg ggg gac tgt cac aat tcc ttt gtg gca ctg aat<br>Asn Thr Asp Gly Leu Gly Asp Cys His Asn Ser Phe Val Ala Leu Asn<br>565 570 575 | 2385 |
| ggg cat tcc agt tcc ctc ttg ccc agc aca acc aca tca gat tcg acg<br>Gly His Ser Ser Ser Leu Leu Pro Ser Thr Thr Thr Ser Asp Ser Thr<br>580 585 590 | 2433 |
| gct caa gag ggg tat gag tct agg gga gga atg ctg gac tgg aag cat<br>Ala Gln Glu Gly Tyr Glu Ser Arg Gly Gly Met Leu Asp Trp Lys His<br>595 600 605 | 2481 |
| ctg ctt gac tca cct gac agc aca gac cct ttg ggg gca gtg tct tcc<br>Leu Leu Asp Ser Pro Asp Ser Thr Asp Pro Leu Gly Ala Val Ser Ser<br>610 615 620 | 2529 |
| cat aat cac caa gac aag aag gga gtg att cgg gaa agt tac ctc aaa<br>His Asn His Gln Asp Lys Lys Gly Val Ile Arg Glu Ser Tyr Leu Lys | 2577 |

-continued

```
                    625                 630                 635                 640
ggc cac gac cag ctg gtt ccc gtc acc ctc ttg gcc att gca gtc atc           2625
Gly His Asp Gln Leu Val Pro Val Thr Leu Leu Ala Ile Ala Val Ile
                        645                 650                 655 ctg gct ttc gtc atg ggg gcc gtc ttc tcg ggc atc acc gtc tac tgc           2673
Leu Ala Phe Val Met Gly Ala Val Phe Ser Gly Ile Thr Val Tyr Cys
                660                 665                 670 gtc tgt gat cat cgg cgc aaa gac gtg gct gtg gtg cag cgc aag gag           2721
Val Cys Asp His Arg Arg Lys Asp Val Ala Val Val Gln Arg Lys Glu
            675                 680                 685 aag gag ctc acc cac tcg cgc cgg ggc tcc atg agc agc gtc acc aag           2769
Lys Glu Leu Thr His Ser Arg Arg Gly Ser Met Ser Ser Val Thr Lys
        690                 695                 700 ctc agc ggc ctc ttt ggg gac act caa tcc aaa gac cca aag ccg gag           2817
Leu Ser Gly Leu Phe Gly Asp Thr Gln Ser Lys Asp Pro Lys Pro Glu
705                 710                 715                 720 gcc atc ctc acg cca ctc atg cac aac ggc aag ctc gcc act ccc ggc           2865
Ala Ile Leu Thr Pro Leu Met His Asn Gly Lys Leu Ala Thr Pro Gly
                725                 730                 735 aac acg gcc aag atg ctc att aaa gca gac cag cac cac ctg gac ctg           2913
Asn Thr Ala Lys Met Leu Ile Lys Ala Asp Gln His His Leu Asp Leu
                740                 745                 750 acg gcc ctc ccc acc cca gag tca acc cca acg ctg cag cag aag cgg           2961
Thr Ala Leu Pro Thr Pro Glu Ser Thr Pro Thr Leu Gln Gln Lys Arg
            755                 760                 765 aag ccc agc cgc ggc agc cgc gag tgg gag agg aac cag aac ctc atc           3009
Lys Pro Ser Arg Gly Ser Arg Glu Trp Glu Arg Asn Gln Asn Leu Ile
        770                 775                 780 aat gcc tgc aca aag gac atg ccc ccc atg ggc tcc cct gtg att ccc           3057
Asn Ala Cys Thr Lys Asp Met Pro Pro Met Gly Ser Pro Val Ile Pro
785                 790                 795                 800 acg gac ctg ccc ctg cgg gcc tcc ccc agc cac atc ccc agc gtg gtg           3105
Thr Asp Leu Pro Leu Arg Ala Ser Pro Ser His Ile Pro Ser Val Val
                805                 810                 815 gtc ctg ccc atc acg cag cag ggc tac cag cat gag tac gtg gac cag           3153
Val Leu Pro Ile Thr Gln Gln Gly Tyr Gln His Glu Tyr Val Asp Gln
                820                 825                 830 ccc aaa atg agc gag gtg gcc cag atg gcg ctg gag gac cag gcc gcc           3201
Pro Lys Met Ser Glu Val Ala Gln Met Ala Leu Glu Asp Gln Ala Ala
            835                 840                 845 aca ctg gag tat aag acc atc aag gaa cat ctc agc agc aag agt ccc           3249
Thr Leu Glu Tyr Lys Thr Ile Lys Glu His Leu Ser Ser Lys Ser Pro
        850                 855                 860 aac cat ggg gtg aac ctt gtg gag aac ctg gac agc ctg ccc ccc aaa           3297
Asn His Gly Val Asn Leu Val Glu Asn Leu Asp Ser Leu Pro Pro Lys
865                 870                 875                 880 gtt cca cag cgg gag gcc tcc ctg ggt ccc ccg gga gcc tcc ctg tct           3345
Val Pro Gln Arg Glu Ala Ser Leu Gly Pro Pro Gly Ala Ser Leu Ser
                885                 890                 895 cag acc ggt cta agc aag cgg ctg gaa atg cac cac tcc tct tcc tac           3393
Gln Thr Gly Leu Ser Lys Arg Leu Glu Met His His Ser Ser Ser Tyr
                900                 905                 910 ggg gtt gac tat aag agg agc tac ccc acg aac tcg ctc acg aga agc           3441
Gly Val Asp Tyr Lys Arg Ser Tyr Pro Thr Asn Ser Leu Thr Arg Ser
            915                 920                 925 cac cag gcc acc act ctc aaa aga aac aac act aac tcc tcc aat tcc           3489
His Gln Ala Thr Thr Leu Lys Arg Asn Asn Thr Asn Ser Ser Asn Ser
        930                 935                 940 tct cac ctc tcc aga aac cag agc ttt ggc agg gga gac aac ccg ccg           3537
```

```
Ser His Leu Ser Arg Asn Gln Ser Phe Gly Arg Gly Asp Asn Pro Pro
945                 950                 955                 960 ccc gcc ccg cag agg gtg gac tcc atc cag gtg cac agc tcc cag cca       3585
Pro Ala Pro Gln Arg Val Asp Ser Ile Gln Val His Ser Ser Gln Pro
                965                 970                 975 tct ggc cag gcc gtg act gtc tcg agg cag ccc agc ctc aac gcc tac       3633
Ser Gly Gln Ala Val Thr Val Ser Arg Gln Pro Ser Leu Asn Ala Tyr
                980                 985                 990 aac tca ctg aca agg tcg ggg ctg aag cgt acg ccc tcg cta aag ccg       3681
Asn Ser Leu Thr Arg Ser Gly Leu Lys Arg Thr Pro Ser Leu Lys Pro
            995                 1000                1005 gac gta ccc ccc aaa cca tcc ttt gct ccc ctt tcc aca tcc atg           3726
Asp Val Pro Pro Lys Pro Ser Phe Ala Pro Leu Ser Thr Ser Met
    1010                1015                1020 aag ccc aat gat gcg tgt aca taa tcccaggggg aggggtcag                  3770
Lys Pro Asn Asp Ala Cys Thr
1025            1030 gtgtcgaacc agcaggcaag gcgaggtgcc cgctcagctc agcaaggttc tcaactgcct     3830
cgagtaccca ccagaccaag aaggcctgcg gc                                   3862

<210> SEQ ID NO 7
<211> LENGTH: 1030
<212> TYPE: PRT
<213> ORGANISM: Homo sapiens

<400> SEQUENCE: 7

Met Arg Ser Glu Ala Leu Leu Leu Tyr Phe Thr Leu Leu His Phe Ala
1               5                   10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45

Asn Thr Thr Gln Arg His Arg Leu Asp Ile Gln Met Ile Met Ile Met
    50                  55                  60

Asn Gly Thr Leu Tyr Ile Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
            100                 105                 110

His Lys Asp Glu Cys His Asn Phe Ile Lys Val Leu Leu Lys Lys Asn
        115                 120                 125

Asp Asp Ala Leu Phe Val Cys Gly Thr Asn Ala Phe Asn Pro Ser Cys
    130                 135                 140

Arg Asn Tyr Lys Met Asp Thr Leu Glu Pro Phe Gly Asp Glu Phe Ser
145                 150                 155                 160

Gly Met Ala Arg Cys Pro Tyr Asp Ala Lys His Ala Asn Val Ala Leu
                165                 170                 175

Phe Ala Asp Gly Lys Leu Tyr Ser Ala Thr Val Thr Asp Phe Leu Ala
            180                 185                 190

Ile Asp Ala Val Ile Tyr Arg Ser Leu Gly Glu Ser Pro Thr Leu Arg
        195                 200                 205

Thr Val Lys His Asp Ser Lys Trp Leu Lys Glu Pro Tyr Phe Val Gln
    210                 215                 220

Ala Val Asp Tyr Gly Asp Tyr Ile Tyr Phe Phe Phe Arg Glu Ile Ala
225                 230                 235                 240
```

```
Val Glu Tyr Asn Thr Met Gly Lys Val Phe Pro Arg Val Ala Gln
                245                 250                 255

Val Cys Lys Asn Asp Met Gly Gly Ser Gln Arg Val Leu Glu Lys Gln
            260                 265                 270

Trp Thr Ser Phe Leu Lys Ala Arg Leu Asn Cys Ser Val Pro Gly Asp
        275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                325                 330                 335

Ser Val Phe Thr Gly Arg Phe Lys Glu Gln Lys Ser Pro Asp Ser Thr
            340                 345                 350

Trp Thr Pro Val Pro Asp Glu Arg Val Pro Lys Pro Arg Pro Gly Cys
        355                 360                 365

Cys Ala Gly Ser Ser Ser Leu Glu Arg Tyr Ala Thr Ser Asn Glu Phe
    370                 375                 380

Pro Asp Asp Thr Leu Asn Phe Ile Lys Thr His Pro Leu Met Asp Glu
385                 390                 395                 400

Ala Val Pro Ser Ile Phe Asn Arg Pro Trp Phe Leu Arg Thr Met Val
                405                 410                 415

Arg Tyr Arg Leu Thr Lys Ile Ala Val Asp Thr Ala Ala Gly Pro Tyr
            420                 425                 430

Gln Asn His Thr Val Val Phe Leu Gly Ser Glu Lys Gly Ile Ile Leu
        435                 440                 445

Lys Phe Leu Ala Arg Ile Gly Asn Ser Gly Phe Leu Asn Asp Ser Leu
    450                 455                 460

Phe Leu Glu Glu Met Ser Val Tyr Asn Ser Glu Lys Cys Ser Tyr Asp
465                 470                 475                 480

Gly Val Glu Asp Lys Arg Ile Met Gly Met Gln Leu Asp Arg Ala Ser
                485                 490                 495

Ser Ser Leu Tyr Val Ala Phe Ser Thr Cys Val Ile Lys Val Pro Leu
            500                 505                 510

Gly Arg Cys Glu Arg His Gly Lys Cys Lys Lys Thr Cys Ile Ala Ser
        515                 520                 525

Arg Asp Pro Tyr Cys Gly Trp Ile Lys Glu Gly Gly Ala Cys Ser His
    530                 535                 540

Leu Ser Pro Asn Ser Arg Leu Thr Phe Glu Gln Asp Ile Glu Arg Gly
545                 550                 555                 560

Asn Thr Asp Gly Leu Gly Asp Cys His Asn Ser Phe Val Ala Leu Asn
                565                 570                 575

Gly His Ser Ser Ser Leu Leu Pro Ser Thr Thr Thr Ser Asp Ser Thr
            580                 585                 590

Ala Gln Glu Gly Tyr Glu Ser Arg Gly Gly Met Leu Asp Trp Lys His
        595                 600                 605

Leu Leu Asp Ser Pro Asp Ser Thr Asp Pro Leu Gly Ala Val Ser Ser
610                 615                 620

His Asn His Gln Asp Lys Lys Gly Val Ile Arg Glu Ser Tyr Leu Lys
625                 630                 635                 640

Gly His Asp Gln Leu Val Pro Val Thr Leu Leu Ala Ile Ala Val Ile
                645                 650                 655
```

-continued

```
Leu Ala Phe Val Met Gly Ala Val Phe Ser Gly Ile Thr Val Tyr Cys
            660                 665                 670

Val Cys Asp His Arg Arg Lys Asp Val Ala Val Val Gln Arg Lys Glu
        675                 680                 685

Lys Glu Leu Thr His Ser Arg Arg Gly Ser Met Ser Ser Val Thr Lys
    690                 695                 700

Leu Ser Gly Leu Phe Gly Asp Thr Gln Ser Lys Asp Pro Lys Pro Glu
705                 710                 715                 720

Ala Ile Leu Thr Pro Leu Met His Asn Gly Lys Leu Ala Thr Pro Gly
                725                 730                 735

Asn Thr Ala Lys Met Leu Ile Lys Ala Asp Gln His His Leu Asp Leu
                740                 745                 750

Thr Ala Leu Pro Thr Pro Glu Ser Thr Pro Thr Leu Gln Gln Lys Arg
            755                 760                 765

Lys Pro Ser Arg Gly Ser Arg Glu Trp Glu Arg Asn Gln Asn Leu Ile
        770                 775                 780

Asn Ala Cys Thr Lys Asp Met Pro Pro Met Gly Ser Pro Val Ile Pro
785                 790                 795                 800

Thr Asp Leu Pro Leu Arg Ala Ser Pro Ser His Ile Pro Ser Val Val
                805                 810                 815

Val Leu Pro Ile Thr Gln Gln Gly Tyr Gln His Glu Tyr Val Asp Gln
            820                 825                 830

Pro Lys Met Ser Glu Val Ala Gln Met Ala Leu Glu Asp Gln Ala Ala
        835                 840                 845

Thr Leu Glu Tyr Lys Thr Ile Lys Glu His Leu Ser Ser Lys Ser Pro
    850                 855                 860

Asn His Gly Val Asn Leu Val Glu Asn Leu Asp Ser Leu Pro Pro Lys
865                 870                 875                 880

Val Pro Gln Arg Glu Ala Ser Leu Gly Pro Pro Gly Ala Ser Leu Ser
                885                 890                 895

Gln Thr Gly Leu Ser Lys Arg Leu Glu Met His His Ser Ser Ser Tyr
            900                 905                 910

Gly Val Asp Tyr Lys Arg Ser Tyr Pro Thr Asn Ser Leu Thr Arg Ser
        915                 920                 925

His Gln Ala Thr Thr Leu Lys Arg Asn Asn Thr Asn Ser Ser Asn Ser
    930                 935                 940

Ser His Leu Ser Arg Asn Gln Ser Phe Gly Arg Gly Asp Asn Pro Pro
945                 950                 955                 960

Pro Ala Pro Gln Arg Val Asp Ser Ile Gln Val His Ser Ser Gln Pro
                965                 970                 975

Ser Gly Gln Ala Val Thr Val Ser Arg Gln Pro Ser Leu Asn Ala Tyr
            980                 985                 990

Asn Ser Leu Thr Arg Ser Gly Leu  Lys Arg Thr Pro Ser  Leu Lys Pro
        995                 1000                 1005

Asp Val  Pro Pro Lys Pro Ser  Phe Ala Pro Leu Ser  Thr Ser Met
    1010                 1015                 1020

Lys Pro  Asn Asp Ala Cys Thr
    1025                 1030

<210> SEQ ID NO 8
<211> LENGTH: 72
<212> TYPE: PRT
<213> ORGANISM: Homo sapiens

<400> SEQUENCE: 8
```

```
Pro Pro Pro Ala Pro Gln Arg Val Asp Ser Ile Gln Val His Ser Ser
1               5                   10                  15

Gln Pro Ser Gly Gln Ala Val Thr Val Ser Arg Gln Pro Ser Leu Asn
            20                  25                  30

Ala Tyr Asn Ser Leu Thr Arg Ser Gly Leu Lys Arg Thr Pro Ser Leu
            35                  40                  45

Lys Pro Asp Val Pro Pro Lys Pro Ser Phe Ala Pro Leu Ser Thr Ser
            50                  55                  60

Met Lys Pro Asn Asp Ala Cys Thr
65                  70

<210> SEQ ID NO 9
<211> LENGTH: 65
<212> TYPE: PRT
<213> ORGANISM: Homo sapiens

<400> SEQUENCE: 9

Pro Pro Pro Gln Pro Gln Arg Lys Pro Gln Val Gln Leu His Val Gln
1               5                   10                  15

Pro Gln Ala Lys Pro His Val Gln Pro Gln Pro Val Ser Ser Ala Asn
            20                  25                  30

Thr Gln Pro Arg Gly Pro Leu Ser Gln Ala Pro Thr Pro Ala Pro Lys
            35                  40                  45

Phe Ala Pro Val Ala Pro Lys Phe Thr Pro Val Val Ser Lys Phe Ser
            50                  55                  60

Pro
65
```

HUMAN SEMAPHORIN 6A-1 (SEMA6A-A), A GENE INVOLVED IN NEURONAL DEVELOPMENT AND REGENERATION MECHANISMS DURING APOPTOSIS, AND ITS USE AS A POTENTIAL DRUG TARGET

PRIOR RELATED APPLICATIONS

This application is the U.S. National Phase filing of International Application PCT/EP99/09215, with an international filing date of Nov. 26, 1999, which claims priority to European Patent Application No. 98 122 441.3 filed Nov. 26, 1998.

The present invention relates to human semaphorin 6A-1 (SEMA6A-1), a novel gene involved in neuronal development and regeneration mechanisms during apoptosis.

Actin binding and filament assembly controlling proteins are essential for cellular events that require a drastic remodelling of cytoskeletal elements during development and apoptosis. Proline-rich proteins of the Ena/VASP family play a crucial role in actin and filament dynamics and have only recently been shown to be clustered to cell surface receptors like Dlar, a tyrosine phosphatase essential for motor axon outgrowth (F. B. Gertler et al., 1996, Cell 87, 227–239; Z. Wills et al., 1999, Neuron 22, 301–312). In the last decade the semaphorins were identified as a protein family displaying secreted or transmembrane-based repulsive guidance cues critically involved in neuronal development (J. G. Culotti and A. L. Kolodkin, Curr. Op. Neurobiol., 6, 81–88).

Therefore, it was an object of the present invention to provide a novel human semaphorin variant.

The invention comprises a nucleic acid coding for human semaphorin 6A-1 comprising:
  (a) the nucleotide sequence shown in SEQ ID NO:1,
  (b) a sequence corresponding to the nucleotide sequence shown in SEQ ID NO:1 within the degeneration of the genetic code, or
  (c) a sequence which hybridizes with the sequences of (a) or/and (b) under stringent conditions.

Surprisingly, the transmembranous human semaphorin 6A-1 ((HSA) SEMA6A-1) is capable of a selective binding to members of the Ena/VASP protein family. (HSA) SEMA6A-1 contains a cytoplasmic stretch at its C-terminal end. This domain shares a striking homology to Zyxin, a protein known to bind Ena/VASP (T. Macalma et al., 1996, JBC 271, 31470–31478; S. Hu and L. F. Reichardt, Neuron 22, 419–422). Thus, the human semaphorin sequence was found to comprise a section which matches with other semaphorin sequences, e.g. murine semaphorin sequences as well as a novel domain at its C-terminal end which is capable of binding to elements attached to the cytoskeleton.

Therefore, the invention further comprises a nucleic acid coding for a binding domain of human semaphorin 6A-1 comprising: (a) the nucleotide sequence shown in SEQ ID NO:3, (b) a sequence corresponding to the nucleotide sequence shown in SEQ ID NO:3 within the degeneration of the genetic code, or (c) a sequence which hybridizes with the sequences of (a) or/and (b) under stringent conditions.

The term "hybridization under stringent conditions" according to the present invention is used as described by Sambrook et al. (Molecular Cloning, A Laboratory Manual, Cold Spring Harbor Laboratory Press (1989), 1.101–1.104). Preferably, a stringent hybridization according to the present invention is given when after washing for an hour with 1×SSC and 0.1% SDS at 50° C., preferably at 55° C., more preferably at 62° C., and most preferably at 68° C., and more preferably for 1 hour with 0.2×SSC and 0.1% SDS at 50° C., preferably at 55° C., more preferably at 62° C., and most preferably at 68° C. a positive hybridization signal is still observed. A nucleotide sequence which hybridizes under such washing conditions with the nucleotide sequence shown in SEQ ID NO:1 or with a nucleotide sequence corresponding thereto within the degeneration of the genetic code is a nucleotide sequence according to the invention.

The nucleic acid according to the invention preferably is in operative association with an expression control sequence that is active in eukaroytic cells, preferably in mammal cells.

The nucleotide sequence according to the invention preferably is a DNA. However, it may also be an RNA or a nucleic acid analog, such as a peptidic nucleic acid.

The nucleic acid according to the invention preferably comprises a sequence having a homology of greater than 80%, preferably greater than 90%, and more preferably greater than 95% and, in particular, greater than 97% to the nucleotide sequence according to SEQ ID NO:1. The term homology as used herein can be defined by the equation $H(\%)=[1-V/X]\cdot 100$, wherein H means homology, X is the total number of nucleobases of the nucleotide sequence according to SEQ ID NO:1 and V is the number of different nucleobases of a comparative sequence with regard to the nucleotide sequence according to SEQ ID NO:1.

The invention further comprises a polypeptide encoded by a nucleic acid according to the invention. Such a polypeptide is, in particular, capable of binding to members of the Ena/VASP protein family. The transmembranous SEMA6A-1 is capable of selectively binding to Evl but not Mena, both members of the Ena/VASP protein family.

The nucleic acids according to the invention can be obtained using known techniques, e.g. using short sections of the nucleotide sequence shown in SEQ ID NO:1 as hybridization probe or/and primer. They can, however, also be produced by chemical synthesis.

The invention further comprises a recombinant vector containing at least one copy of the nucleic acid according to the invention. This vector may be a prokaryotic or a eukaryotic vector which contains the nucleic acid according to the invention under the control of an expression signal (promoter, operator, enhancer etc.). Examples of prokaryotic vectors are chromosomal vectors such as bacteriophages and extra-chromosomal vectors such as plasmids, circulary plasmid vectors being particularly preferred. Prokaryotic vectors useful according to the present invention are, e.g., described in Sambrook et al., supra, chapter 1–4.

More preferably, the vector according to the invention is a eukaryotic vector, in particular a vector for mammal cells. Most preferred are vectors suitable for gene therapy, such as retrovirus, modified adenovirus or adeno-associated virus. Such vectors are known to the man skilled in the art of molecular biology and gene therapy and are also described in Sambrook et al., supra, chapter 16.

In addition to the polypeptide encoded by the nucleic acid of SEQ ID NO:1 or SEQ ID NO:3, the invention also relates to polypeptides differing therefrom by substitutions, deletions or/and insertions of single amino acids or short amino acid sections. The polypeptide is obtainable by expression of the nucleic acid sequence in a suitable expression system (cf. Sambrook et al., supra).

The polypeptide encoded by SEQ ID NO:1 is (HSA) SEMA6A-1, a new semaphorin variant containing a Zyxin-like domain that binds to the Ena/VASP-like protein (Evl). In particular, the semaphorins are a protein family displaying secreted or transmembrane-based repulsive guidance cues critically involved in neuronal development. The polypeptide encoded by SEQ ID NO:3 is a binding domain. This domain can bind selectively to Evl, a member of the Ena/VASP protein family. It may be particularly favorable to combine this binding domain with other proteins having known functionality to give a fusion protein. This binding domain can be used advantageously, alone or as part of a fusion protein, as a means for screening and as a diagnostic and therapeutic target.

The invention further comprises a cell transformed with a nucleic acid or a vector according to the invention. The cell may be a eukaryotic or a prokaryotic cell, eukaryotic cells being preferred.

The present invention also comprises the use of the polypeptide or fragments thereof as immunogen for the production of antibodies. Standard protocols for obtaining antibodies may be used.

The present invention also comprises a pharmaceutical composition comprising a nucleic acid, modified nucleic acid, vector, cell, polypeptide or antibody as defined herein as active component.

The pharmaceutical composition may comprise pharmaceutically acceptable carriers, vehicles and/or additives and additional active components, if desired. The pharmaceutical composition can be used for diagnostic purposes or for the production of therapeutic agents. Particularly preferred is the use as a therapeutic agent for the modulation of the immune system.

Since the human semaphorin 6A-1 gene is involved in neuronal development and regeneration mechanisms during apoptosis, this gene can be used to design drug target structures. Members of the semaphorin gene family act as guidance signals and regulatory molecules during neuronal development. Besides its role in development, semaphorin has essential functions in the immune system. Semaphorin can also be linked to potential cancer, drug resistance and disease genes.

On the basis of a phylogenetic approach, the semaphorin gene family is currently distinguished into eight classes containing invertebrate (classes 1, 2) and vertebrate proteins (classes 3–7). Consistent with this nomenclature, the newly identified semaphorin is grouped into class 6 as human semaphorin 6A-1.

RNA expression studies have revealed SEMA6A-1 expression in areas consistent with a role of SEMA6A-1 as a guidance and regulatory signal during development and regeneration. Specialized domains in the cytoplasmic tail of the SEMA6A-1 gene product containing cytoskeletal binding elements show that SEMA6A-1 is also involved in differentiation, cytoskeletal stabilization and plasticity.

Finally, the invention is also directed to the use of the herein described pharmaceutical compositions for effecting differentiation, cytoskeletal stabilization and/or plasticity.

The invention is further described by the appended figures and examples, wherein FIG. 1 shows SEQ ID NO:1, the coding nucleotide sequence of the human semaphorin 6A-1 gene.

FIG. 2 shows the nucleotide sequence of the human semaphorin 6A-1 gene as well as the derived amino acid sequence thereof;

Figure 4:
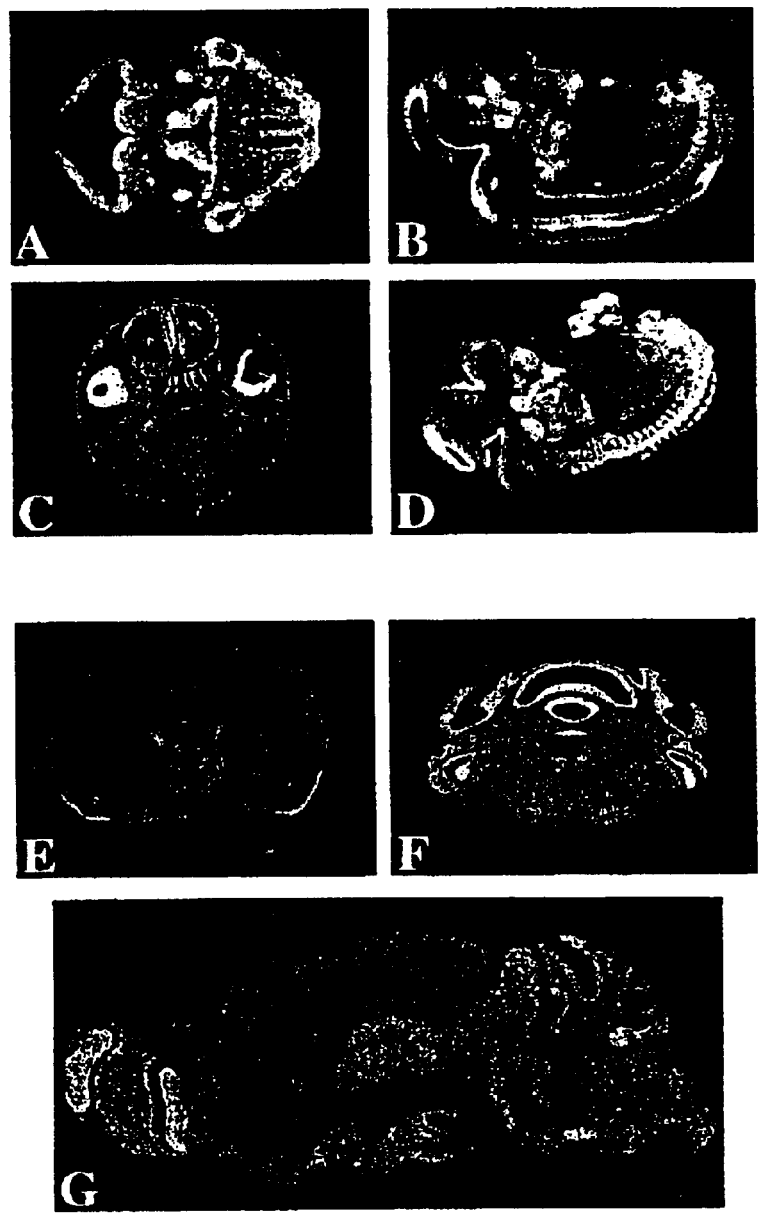
Figure 5:
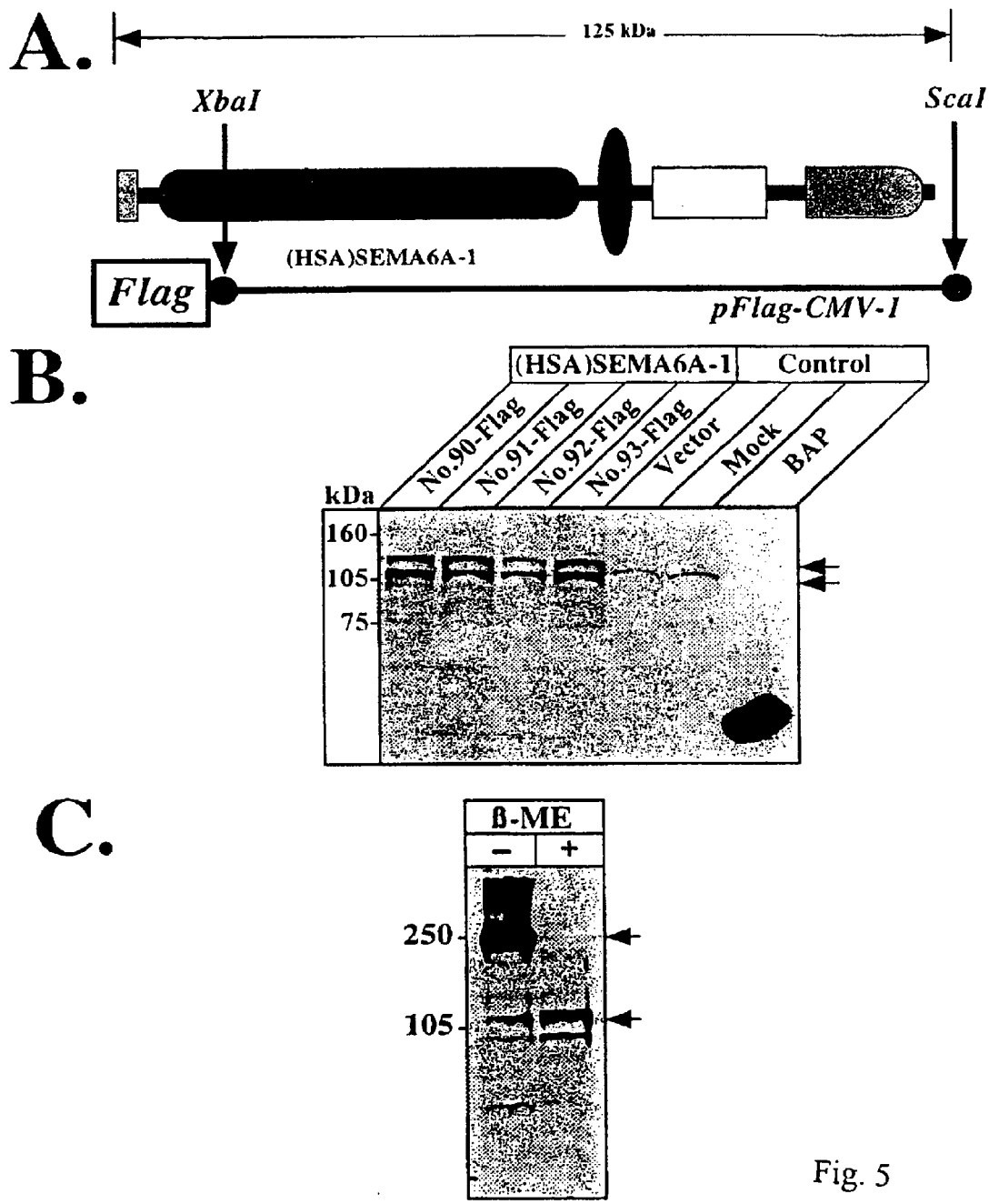
Figure 8:
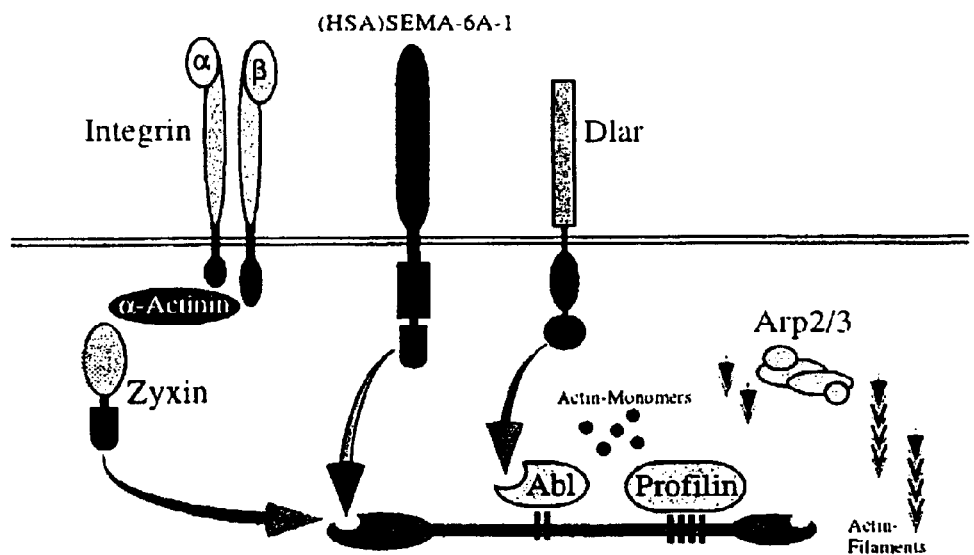

FIG. 4 shows the (MMU)Sema6A-1 distribution in mouse adult and embryonic tissues revealed by in-situ hybridizations of embryonic (panels A–D) and adult (panels E–G) tissues, showing dominant expression in embryonic brain stem (panels A, B, and D), optic precursors (panels A and C), spinal cord (panels B and D), limb (panel B), and adult piriform cortex (panel E) cerebellar regions (panels F and G) and olfactory bulb (panel G);

FIG. 5 shows, in panel A, a graphical overview on the domain structure of (HAS)SEMA6A-1 and the subcloning strategy; and, in panels B and C, Western blots displaying the protein size and its dimerization abilities;

FIG. 6 shows a sequence alignment between SEMA6A-1 and Zyxin, wherein FIG. 6a is a SEMA6A-1 sequence SEQ ID NO:8, of a a binding domain, and 6b shows SEQ ID NO:9, a sequence of Zyxin;

FIG. 7 shows immunoprecipitation of (HAS)SEMA6A-1 with α-Evl and α-Mena antibodies. In panel A: (α-Evl); Vector only (lane 1), pFlagSEMA6A-1 (lane 2), HT22 supplemented with purified SEMA6A-1 protein (lane 3), pFlagSEMA6A-1 precipitation using only protein A beads (lane 4), control detection of pFlagSEMA6A-1 transfected cells (lane 5), SEMA6A-1 purified control (lane 6), untransfected HT22 control (lane 7), Evl control in HT22 (lane 8); In panel B: (α-Mena): Vector only (lane 1), pFlagSEMA6A-1 (lane 2), HT22 supplemented with purified SEMA6A-1 protein (lane 3), control detection of pFlagSEMA6A-1 transfected cells (lane 4);

FIG. 8 gives a graphical overview on the known Ena/VASP interacting proteins like Zyxin, Dlar and (HSA) SEMA6A-1.

EXAMPLES

Example 1

Cloning, Genomic Localization and Tissue Distribution of (HSA)SEMA6A-1

To identify and isolate repulsive guidance cues that might be involved in neuronal apoptosis a low stringency PCR-approach on cDNA from the human neuroblastoma cell line SK-N-MC was performed and a fragment of (HSA) SEMA6A-1 was amplified. This fragment was used to screen a human 1-ZAP Express cDNA library. Sequencing of 4 isolated clones revealed an ORF of 3093 bp referring to a protein of 1030 amino acids in total length with a predicted size of 135 kDa. (FIG. 2: Nucleic acid sequence and deduced amino acid sequence).

Database searches identified 43 unordered sequences (Genbank Acc.-No. AC008524) and a mapped genomic survey sequence (Genbank Acc.-No. AB002453) of human chromosome 5 localizing the gene to 5q21–22. Gaps between the genomic sequences were closed by PCR on human genomic DNA and subsequent sequencing.

The (hsa)sema6A-1 gene covers 45 kb of genomic sequence and consists of 18 exons including 1 untranslated exon at the 3'-end (see FIG. 2).

Example 2

Similarity and Domain Structure of (HSA)SEMA6A-1

Database searches revealed that SEMA6A-1 (1030aa) has a relatively high similarity to its murine ortholog Sema6A-1 (869aa) within the overlapping region consisting of 869aa. The existence of an additional cytoplasmic domain prompted us to name the new protein SEMA6A-1. This unique domain shares a 33% identity (49% similarity) to Zyxin, a proline-rich protein present at focal adhesion points and capable of binding to members of the Ena/VASP family. Binding of Zyxin to Ena/VASP occurs via a peptide stretch displaying the sequence DFPPPP (K. E. Prehoda et al., 1999, Cell 97, 471–480). (HSA)SEMA6A-1 contains two potential binding motifs (aa 858–962 (DNPPP) and aa 1010–1015 (DVPPKP) in its Zyxin homologous domain that are similar to the above-mentioned motif.

Figure 3:
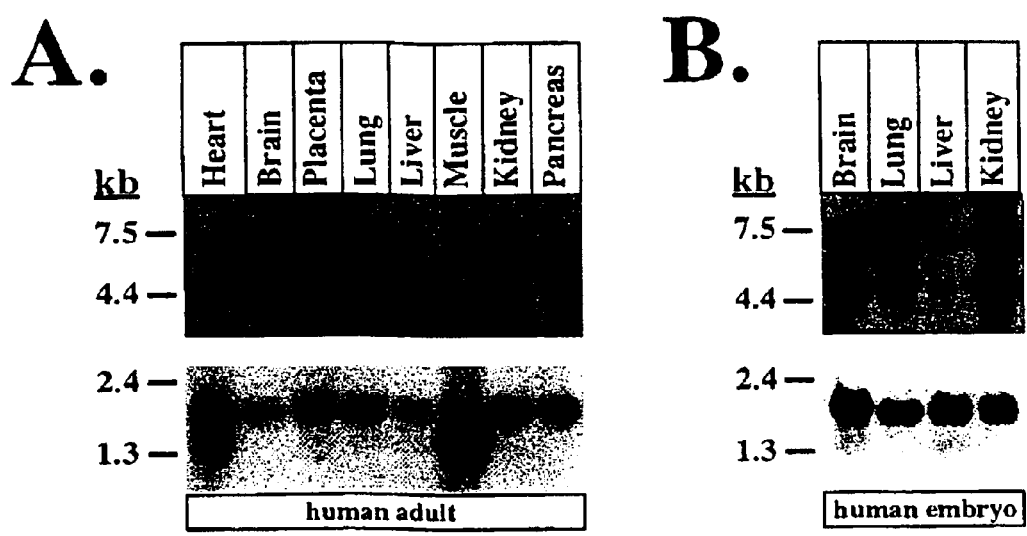
FIG. 3 shows the tissue distribution of (HAS)SEMA6A-1 revealed by Northern blot hybridizations of human embryo brain, lung, liver, kidney (panel A) and human adult heart, brain, placenta, lung, liver, skeletal muscle, kidney and pancreas tissue, (panel B) respectively.

Example 3
Tissue Distribution of (HSA)SEMA6A-1 Revealed by Northern Blot and In Situ Hybridization Northern blot hybridizations of poly $A^+$ RNA of human adult and embryonic tissues detected two transcripts in the molecular range of 4.5 kb and 7 kb. Highest levels of detection were present in embryonic brain and kidney, moderate expression in lung and virtually no expression in liver. Compared to embryonic levels there was observed a clear reduction of expression of (HSA)SEMA6A-1 in adult tissues with the exception of placenta. In situ hybridizations in mouse embryo revealed a distinct expression throughout the whole embryo that is restricted to nervous system areas. These results indicate a general role of this protein in development and are shown in FIGS. 3 and 4: FIG. 3 shows the human Northern blots. FIG. 4 displays in situ hybridizations of embryonic (A, B, C, D) and adult (E, F, G) tissues. Notify the dominant expression in embryonic brain stem (A, B, D), optic precursors (A, C), spinal cord (B, D) and limb (B). High expression levels in adult regions are maintained in piriform cortex (E), cerebellar regions (F, G) and olfactory bulb (G).

Example 4
Expression of (HSA)SEMA6A-1 in Mammalian Cell Lines

In order to show that Ena/VASP proteins might be potential intracellular binding partners for (HAS) SEMA6A-1 (see FIG. 6, Alignment of (HAS)SEMA6A-1 (SEQ ID NO:8) and Zyxin (SEQ ID NO:(9)) and the (HAS) SEMA6A-1 and Ena/VASP-like proteins might be interacting partners a XbaI/ScaI fragment of the SEMA6A-1 clone covering the full length protein sequence only lacking the signal sequence was subcloned into the pFLAGE-CMV-1 vector. This vector allows rapid detection of the expressed fusion protein through the N-terminal Flag-Taq fused to the protein. Immunoblotting of the tagged protein (Flag-SEMA6A-1) displayed a protein sized of 125 kDa which closely corresponds to the predicted protein size. Expression in a human cell line (HEK293) and in a clonal mouse hippocampal cell line (HT22) followed by immunofluorescent analysis revealed that SEMA6A-1 is targeted to the cell surface and colocalizes with Evl and Mena, indicating a possible interaction between these proteins (see FIG. 5, showing, in panel A, a graphical overview on the domain structure of (HAS)SEMA6A-1 and the subcloning strategy. In addition, Western blots displaying the protein size and its dimerization abilities are shown in panels B and C).

Example 5
Immunoprecipitation of (HSA)SEMA6A-1

Using antibodies specific for Mena and Evl Flag-SEMA6A-1 was immunoprecipitated from Triton X-100 extracts of transfected HEK239 and HT22 cells. The precipitate was separated by SDS-PAGE, and subsequent immunoblotting with the monoclonal anti-Flag antibody revealed that Flag-SEMA6A-1 co-immunoprecipitates with Evl but not Mena. To confirm this interaction Flag-SEMA6A-1 was purified from transfected HEK293 cells on an anti-Flag affinity column and the Triton X-100 extract of untransfected HT22 cells was supplemented with the purified protein, followed by immunoprecipiation of the protein complex using the α-Evl antibody. Immunoblotting again revealed that FlagSEMA6A-1 co-precipitates Evl. FIG. 7 shows the immunoprecipitation experiments using the α-Evl- and α-Mena antibodies.

What is claimed is:

1. An isolated protein comprising a protein encoded by SEQ ID NO: 1.

2. An isolated protein consisting of a protein encoded by SEQ ID NO: 3.

3. An isolated protein comprising the amino acid sequence SEQ ID NO: 2.

4. A composition comprising the protein of claim 3 and a pharmaceutically acceptable carrier.

5. An isolated protein consisting of the amino acid sequence SEQ ID NO: 4.

6. A composition comprising the protein of claim 5 and a pharmaceutically acceptable carrier.

7. An isolated protein comprising a protein encoded by the nucleic acid sequence coding for human semaphorin 6A-1 comprising:

(a) the nucleotide sequence shown in SEQ ID NO: 1, or b) a sequence which hybridizes with the sequences of (a) under the following stringent conditions:

(i) 1×SSC and 0.1% SDS at 62° C.

with the proviso that it contains a nucleic acid coding for a binding domain of human semaphorin 6A-1.

8. A composition comprising the protein of claim 7 and a pharmaceutically acceptable carrier.

* * * * *